(12) United States Patent
Stager et al.

(10) Patent No.: US 10,405,855 B2
(45) Date of Patent: Sep. 10, 2019

(54) FIRING CIRCUIT FOR SURGICAL STAPLER

(71) Applicant: Ethicon Endo-Surgery, LLC, Guaynabo, PR (US)

(72) Inventors: William R. Stager, Oakwood, OH (US); Matthew H. Bolton, West Chester, OH (US); Christopher C. Miller, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 438 days.

(21) Appl. No.: 14/751,277

(22) Filed: Jun. 26, 2015

(65) Prior Publication Data

US 2016/0374673 A1 Dec. 29, 2016

(51) Int. Cl.
*A61B 17/064* (2006.01)
*A61B 17/115* (2006.01)
(Continued)

(52) U.S. Cl.
CPC ........ *A61B 17/0644* (2013.01); *A61B 17/068* (2013.01); *A61B 17/1155* (2013.01);
(Continued)

(58) Field of Classification Search
CPC ............ A61B 17/07207; A61B 17/068; A61B 17/064; A61B 17/0644; A61B 17/1155;
(Continued)

(56) References Cited

U.S. PATENT DOCUMENTS 5,205,459 A  4/1993 Brinkerhoff et al.
5,271,544 A  12/1993 Fox et al.
(Continued)

FOREIGN PATENT DOCUMENTS

EP  1 813 207 A1  8/2007
EP  1918071 A2 *  5/2008 ........... B25B 21/026
(Continued)

OTHER PUBLICATIONS

European Search Report and Written Opinion dated Feb. 16, 2017 for Application No. EP 16176148.1, 11 pgs.
(Continued)

*Primary Examiner* — Robert F Long
(74) *Attorney, Agent, or Firm* — Frost Brown Todd LLC

(57) ABSTRACT

A surgical instrument includes a stapling head assembly, an anvil, a firing assembly, a motor, a user input feature, and an electrical circuit. The firing assembly actuates the stapling head assembly to drive an annular array of staples through tissue toward the anvil. The motor actuates the firing assembly through an actuation stroke to thereby actuate the stapling head assembly. The electrical circuit includes a trigger switch and an electrical latching feature. The trigger transitions from an open state to a closed state in response to the user input feature transitioning from a non-actuated state to an actuated state. The electrical circuit activates the motor in response to closure of the trigger switch. The electrical latching feature maintains activation of the motor to complete the actuation stroke even if the trigger switch is transitioned back to the open state before completion of the actuation stroke.

20 Claims, 37 Drawing Sheets

(51) Int. Cl.
*A61B 17/068* (2006.01)
*A61B 17/00* (2006.01)
*A61B 90/00* (2016.01)

(52) U.S. Cl.
CPC .............. *A61B 2017/00119* (2013.01); *A61B 2017/00128* (2013.01); *A61B 2017/00367* (2013.01); *A61B 2017/00398* (2013.01); *A61B 2017/00734* (2013.01); *A61B 2090/0811* (2016.02)

(58) Field of Classification Search
CPC .. A61B 2090/0811; A61B 2017/00119; A61B 2017/00734; A61B 2017/00398; A61B 2017/00128; A61B 2017/00367
USPC ............................................ 227/175.1–182.1
See application file for complete search history.

(56) References Cited

U.S. PATENT DOCUMENTS

| | | | |
|---|---|---|---|
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,533,661 A | 7/1996 | Main et al. | |
| 5,862,972 A * | 1/1999 | Green | A61B 17/0684 227/175.1 |
| 6,945,444 B2 | 9/2005 | Gresham et al. | |
| 7,794,475 B2 | 9/2010 | Hess et al. | |
| 8,408,439 B2 | 4/2013 | Huang et al. | |
| 8,453,914 B2 | 6/2013 | Laurent et al. | |
| 8,910,847 B2 | 12/2014 | Nalagatla et al. | |
| 9,005,230 B2 * | 4/2015 | Yates | A61B 17/068 606/180 |
| 9,161,803 B2 | 10/2015 | Yates et al. | |
| 2008/0223894 A1 * | 9/2008 | Cruise | B25C 1/008 227/2 |
| 2010/0076474 A1 * | 3/2010 | Yates | A61B 17/07207 606/170 |
| 2011/0006101 A1 * | 1/2011 | Hall | A61B 17/07207 227/175.2 |
| 2011/0022032 A1 * | 1/2011 | Zemlok | A61B 17/07207 606/1 |
| 2011/0132959 A1 * | 6/2011 | Hlinka | B25C 1/008 227/8 |
| 2012/0061447 A1 * | 3/2012 | Williams | A61B 17/115 227/175.1 |
| 2014/0144968 A1 | 5/2014 | Shelton | |
| 2014/0144969 A1 | 5/2014 | Scheib et al. | |
| 2014/0151429 A1 | 6/2014 | Scheib et al. | |
| 2014/0151430 A1 | 6/2014 | Scheib et al. | |
| 2014/0158747 A1 | 6/2014 | Measamer et al. | |
| 2014/0166717 A1 | 6/2014 | Swayze et al. | |
| 2014/0166718 A1 | 6/2014 | Swayze et al. | |
| 2014/0166728 A1 | 6/2014 | Swayze et al. | |
| 2015/0083772 A1 | 3/2015 | Miller et al. | |
| 2015/0083773 A1 | 3/2015 | Measamer et al. | |
| 2015/0083774 A1 | 3/2015 | Measamer et al. | |
| 2015/0083775 A1 | 3/2015 | Leimbach et al. | |
| 2015/0272575 A1 | 10/2015 | Leimbach et al. | |
| 2015/0309640 A1 * | 10/2015 | Vuckovic | G06F 3/041 173/1 |
| 2016/0374665 A1 * | 12/2016 | DiNardo | A61B 17/068 227/175.2 |
| 2016/0374672 A1 * | 12/2016 | Bear | A61B 17/1155 606/219 |
| 2016/0374678 A1 * | 12/2016 | Becerra | A61B 17/07207 227/177.1 |
| 2016/0374681 A1 | 12/2016 | Miller et al. | |
| 2017/0258471 A1 * | 9/2017 | DiNardo | A61B 17/1155 |

FOREIGN PATENT DOCUMENTS

| | | |
|---|---|---|
| EP | 2 772 206 A2 | 9/2014 |
| WO | WO 2007/137304 A2 | 11/2007 |
| WO | WO 2015/042378 A2 | 3/2015 |

OTHER PUBLICATIONS

U.S. Appl. No. 14/751,247, filed Jun. 26, 2015.
U.S. Appl. No. 14/751,231, filed Jun. 26, 2015.
U.S. Appl. No. 14/751,517, filed Jun. 26, 2015.
U.S. Appl. No. 14/751,406, filed Jun. 26, 2015.
International Search Report and Written Opinion dated Oct. 10, 2016 for Application No. PCT/US2016/038878.

* cited by examiner

FIRING CIRCUIT FOR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
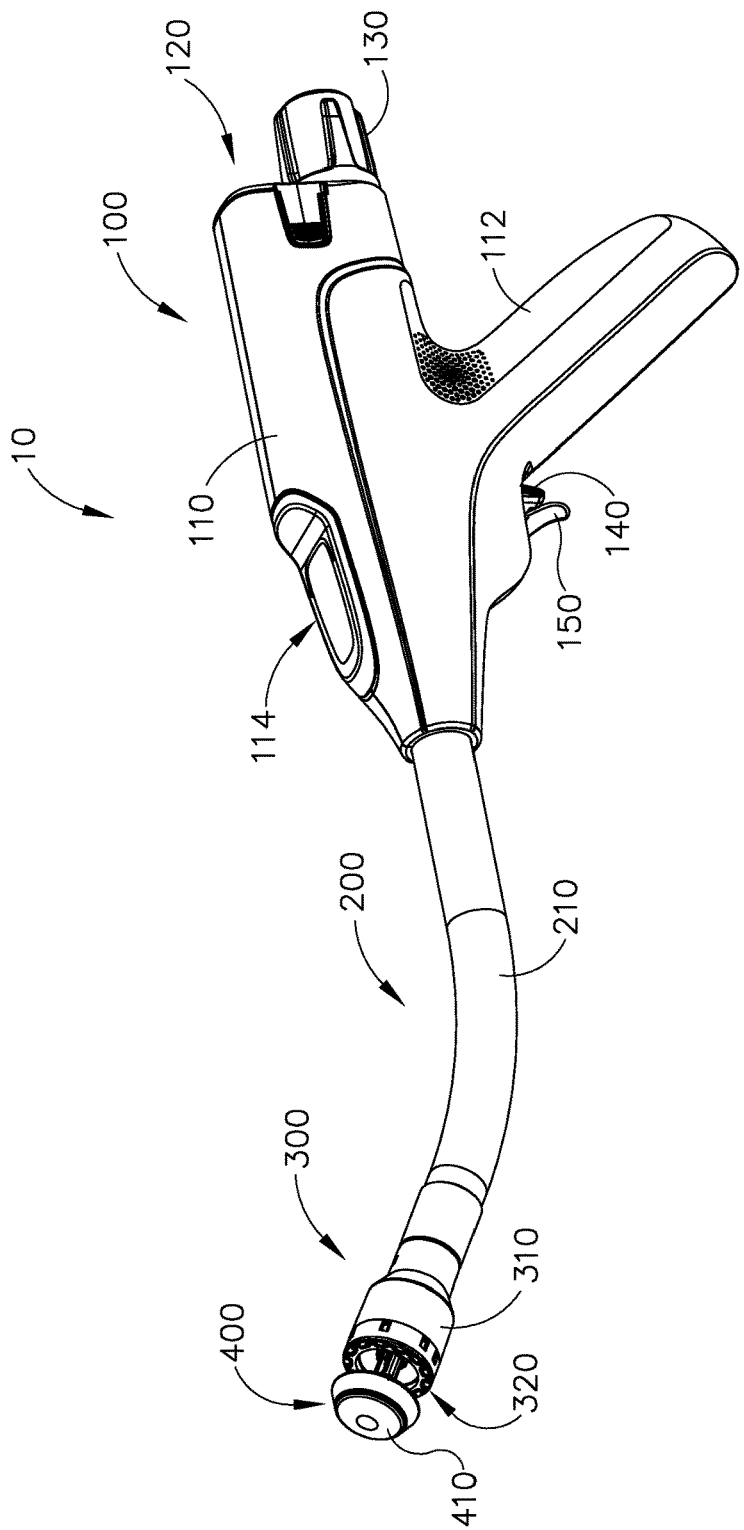
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview Of Exemplary Circular Stapling Surgical Instrument

Figure 2:
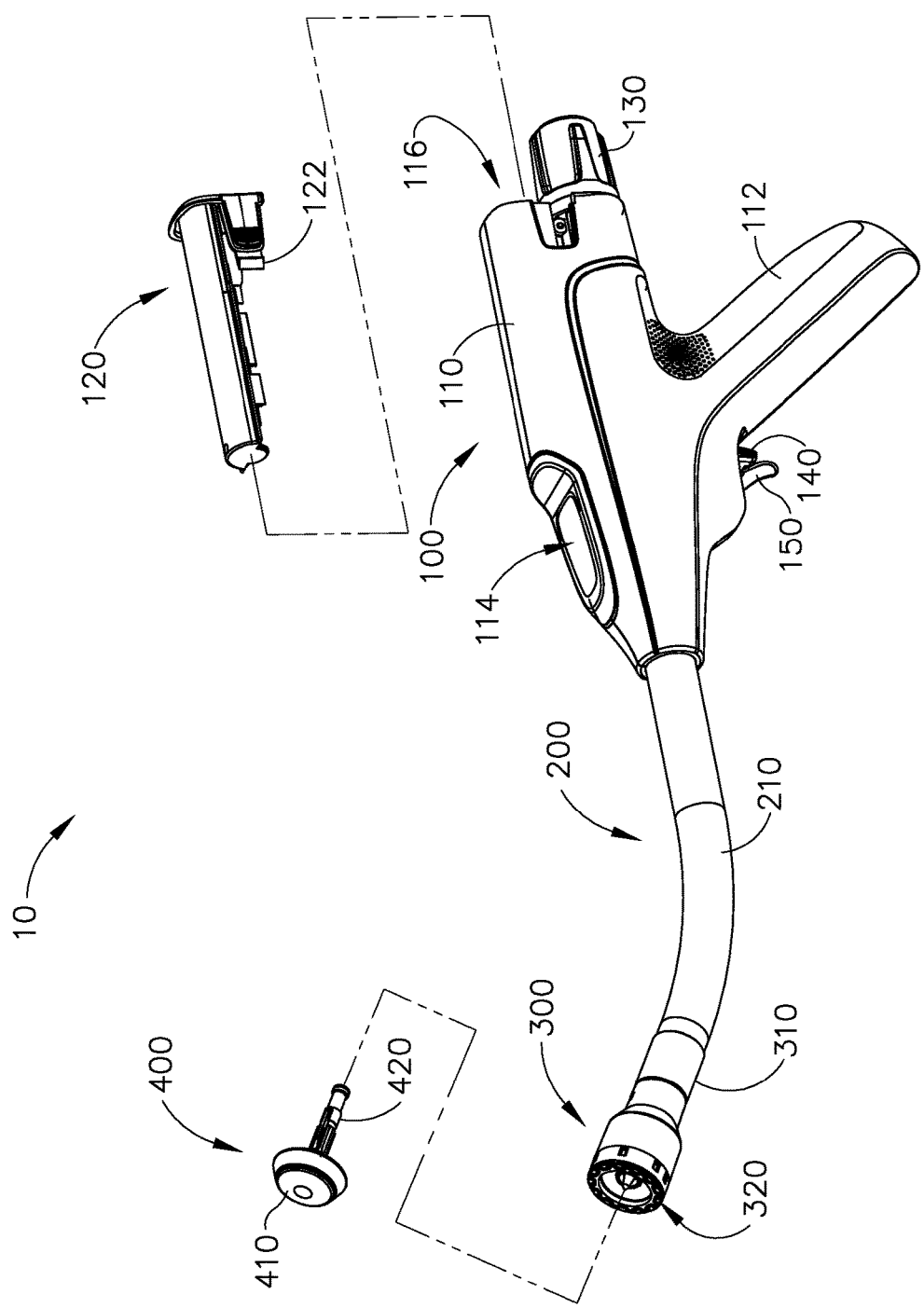
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a user input feature in the form of a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
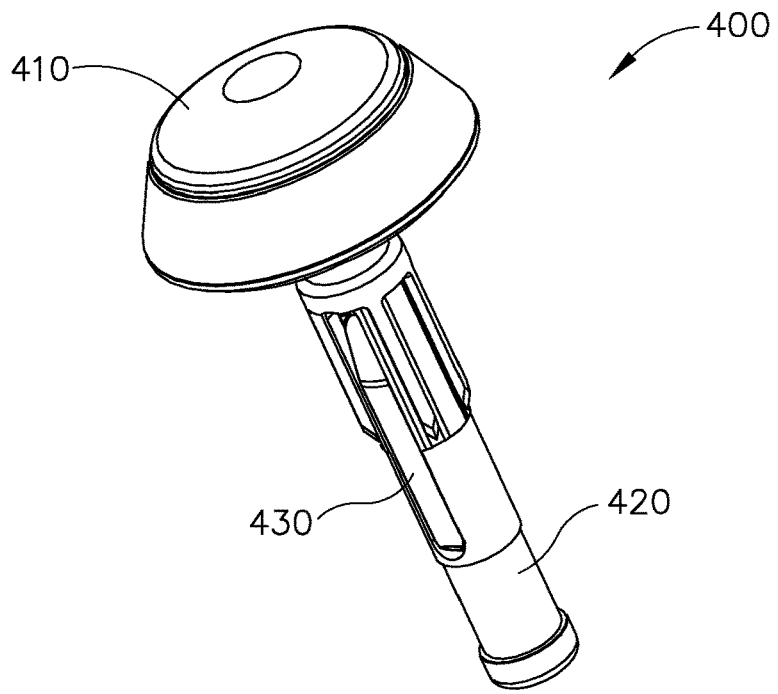
FIG. 3 depicts a perspective view of the anvil of the circular stapler of FIG. 1.
Figure 4:
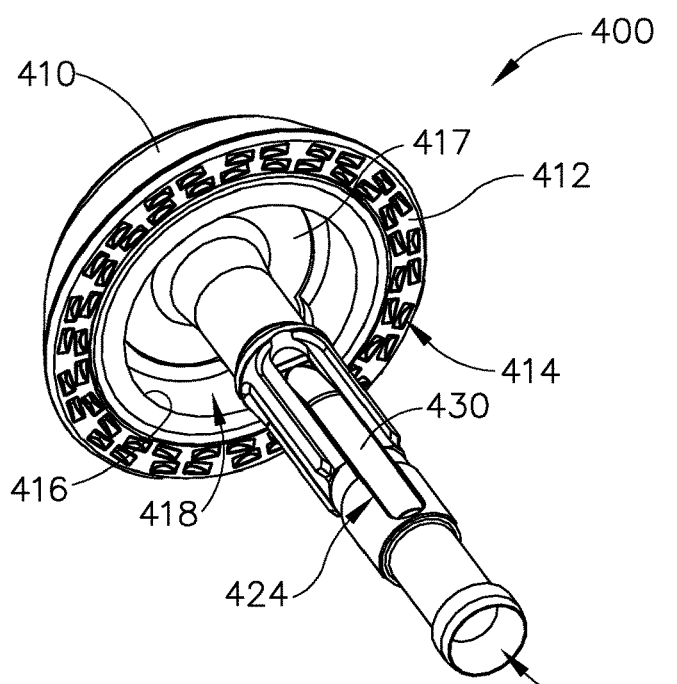
FIG. 4 depicts another perspective view of the anvil of FIG. 3.
Figure 5:
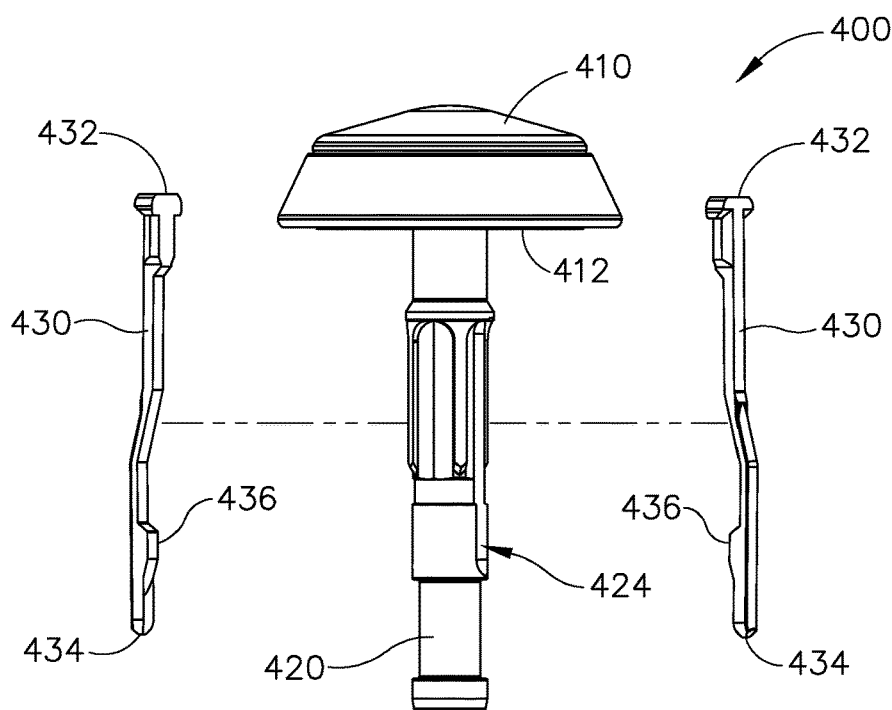
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

B. Exemplary Stapling Head Assembly

Figure 6:
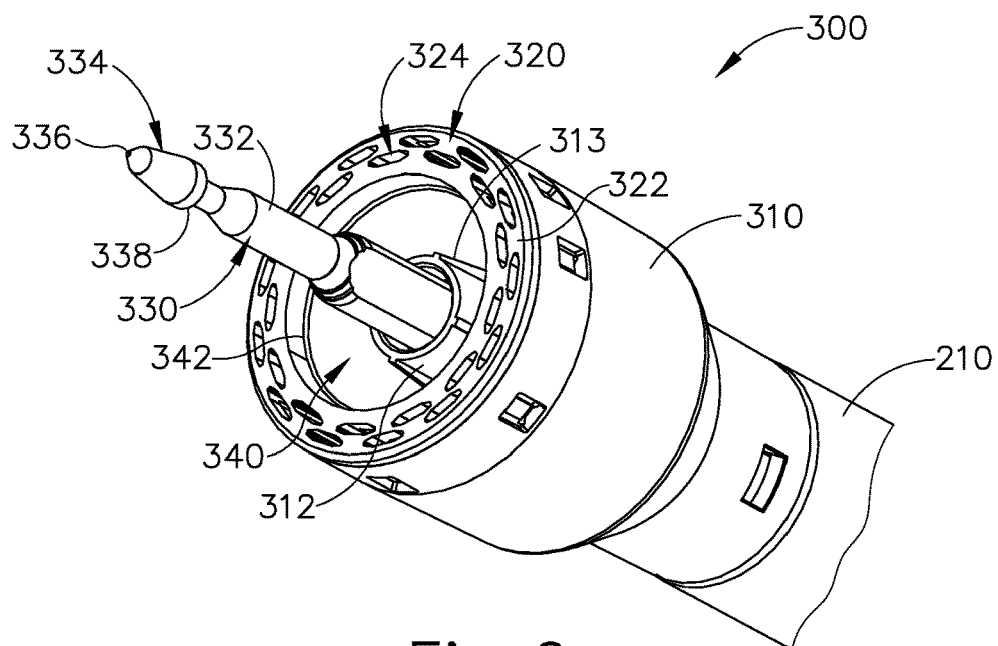
FIG. 6 depicts a perspective view of the stapling head assembly of the circular stapler of FIG. 1.
Figure 7:
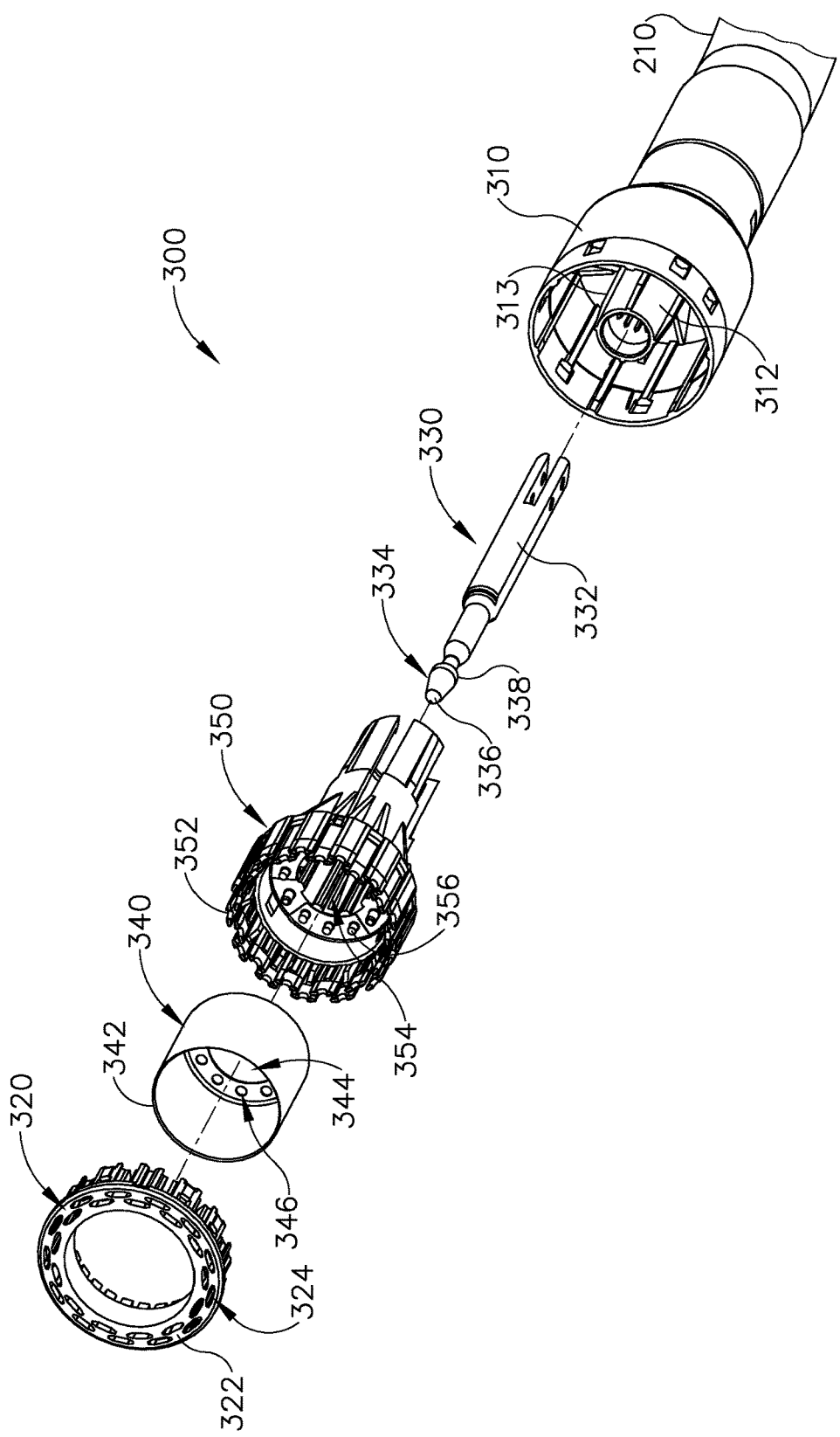
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

C. Exemplary Shaft Assembly

Figure 8:
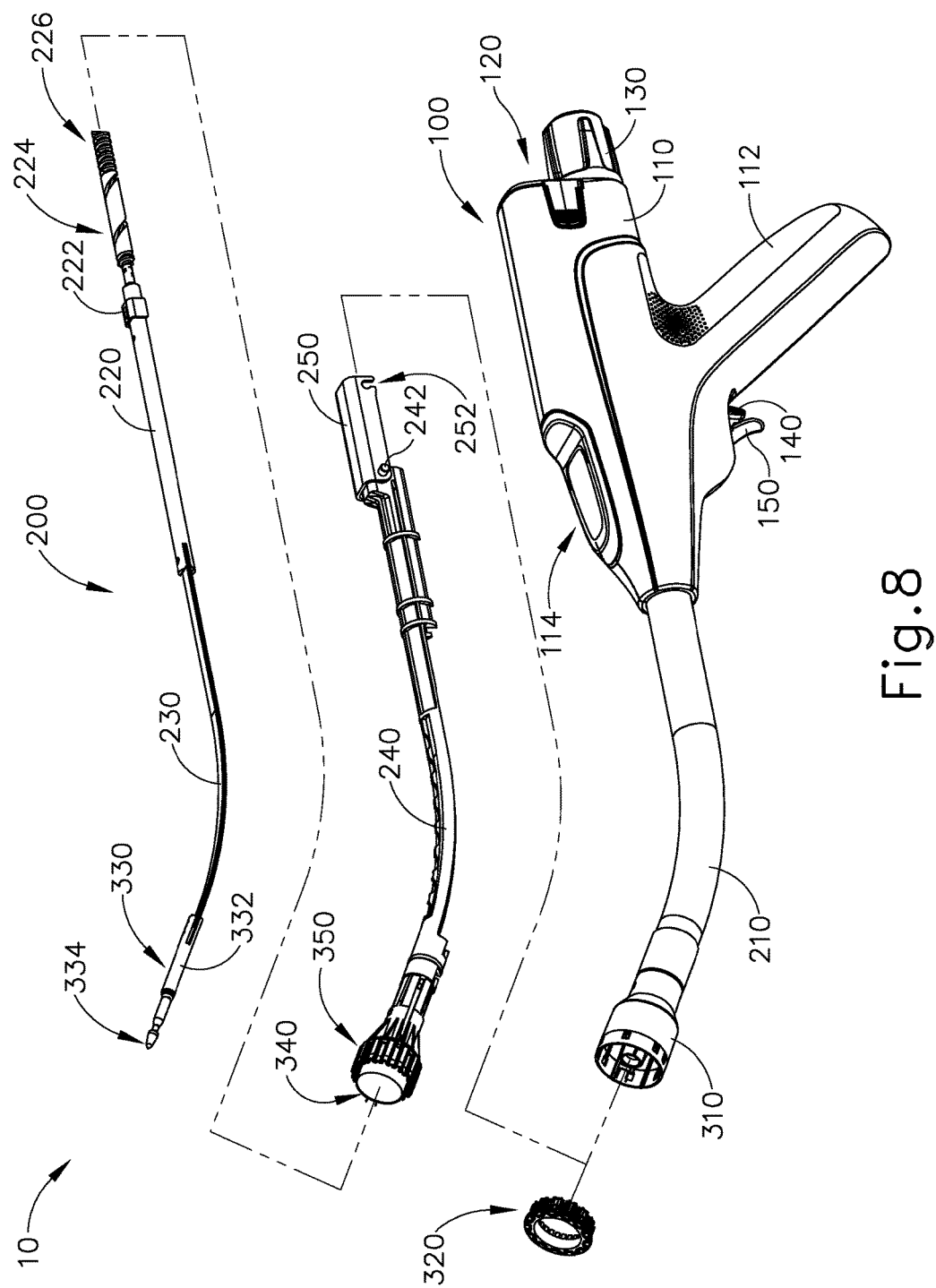
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847, the disclosures of which are incorporated by reference herein. Still other suitable configurations will be apparent to one of ordinary skill in the art in view of the teachings herein.

D. Exemplary Actuator Handle Assembly

Figure 9:
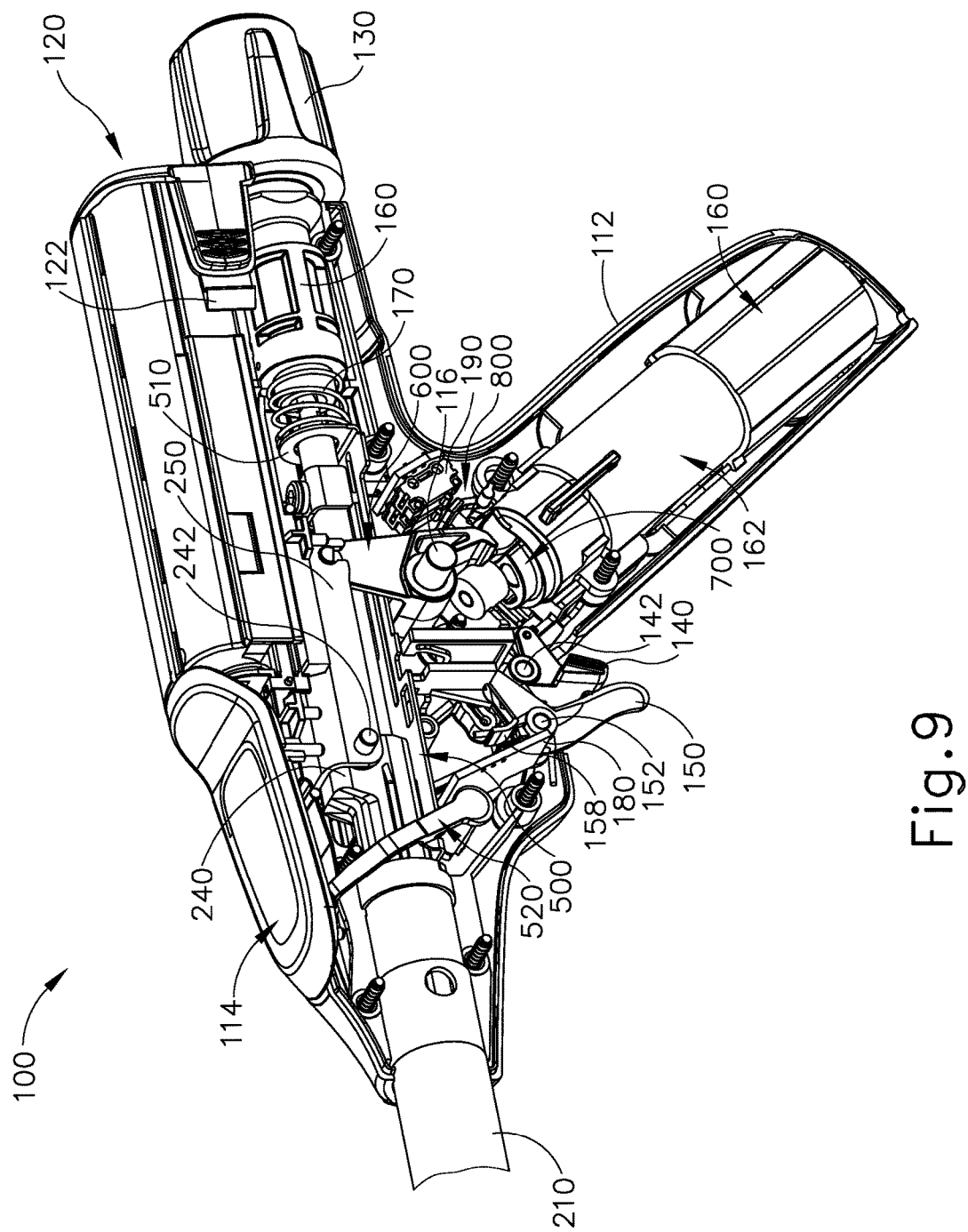
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
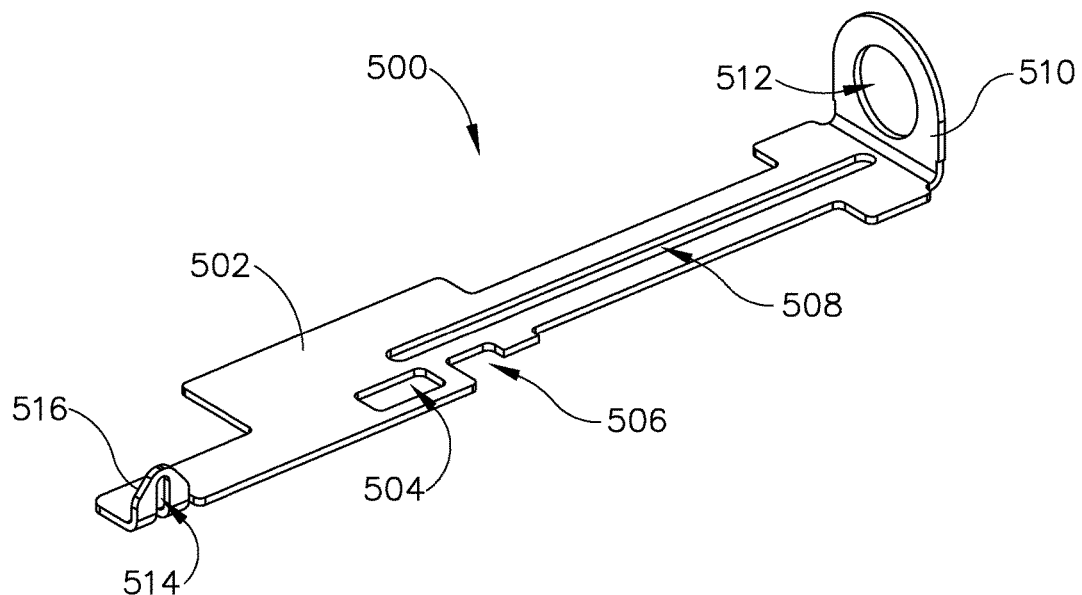
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
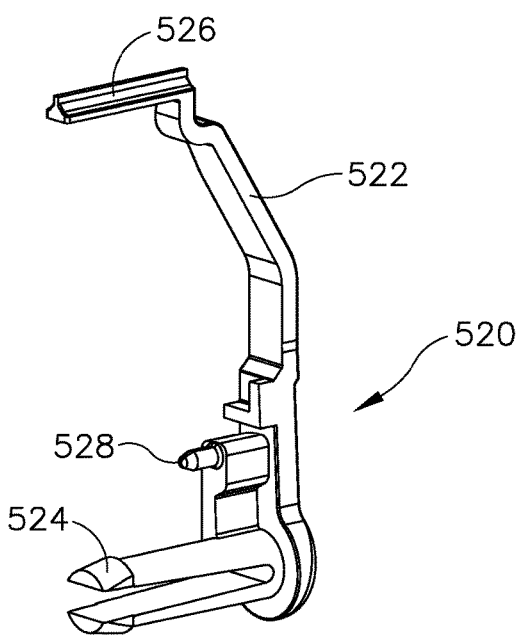
FIG. 11 depicts a perspective view of an indicator member of the handle assembly of FIG. 9.
Figure 12A:
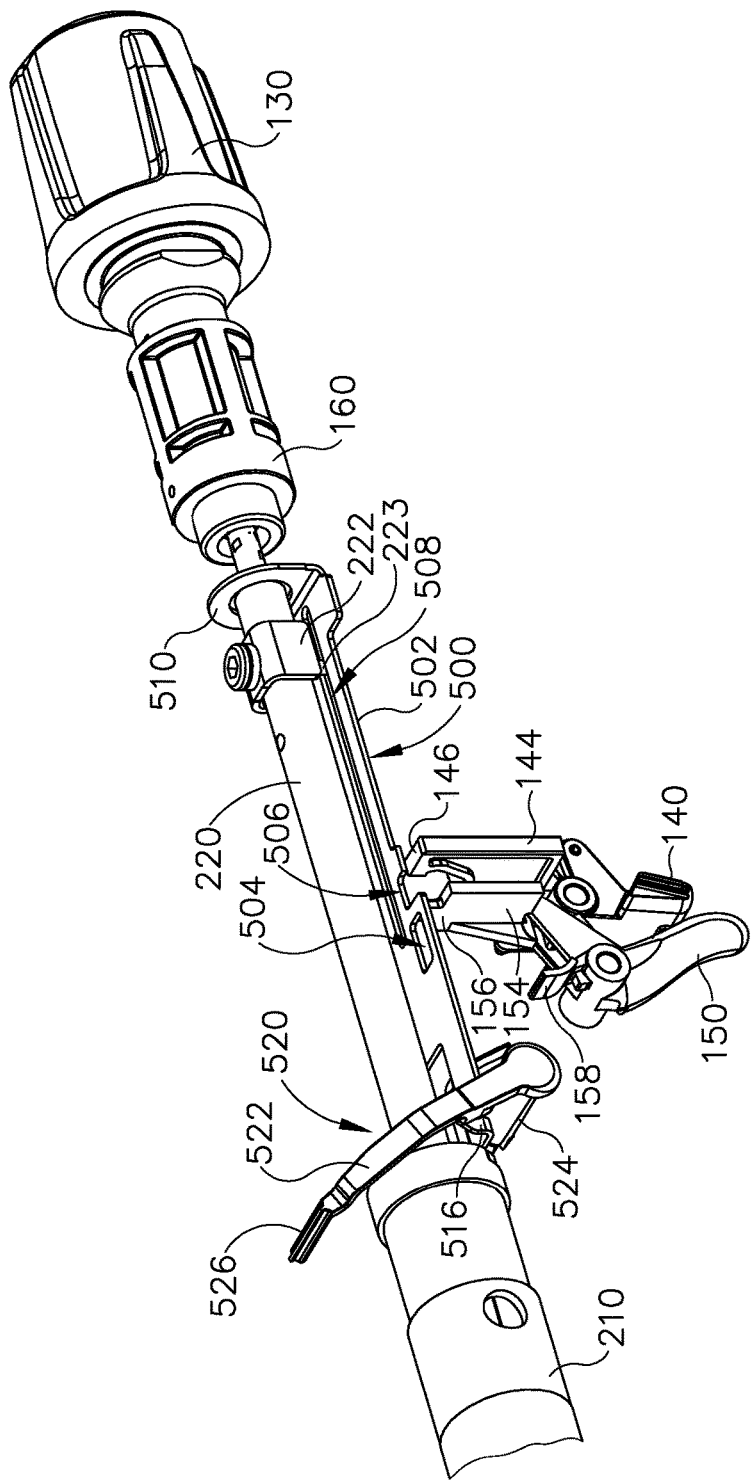
FIG. 12A depicts a perspective view of an anvil actuation assembly of the circular stapler of FIG. 1, an actuation rod in a first position.
Figure 12B:
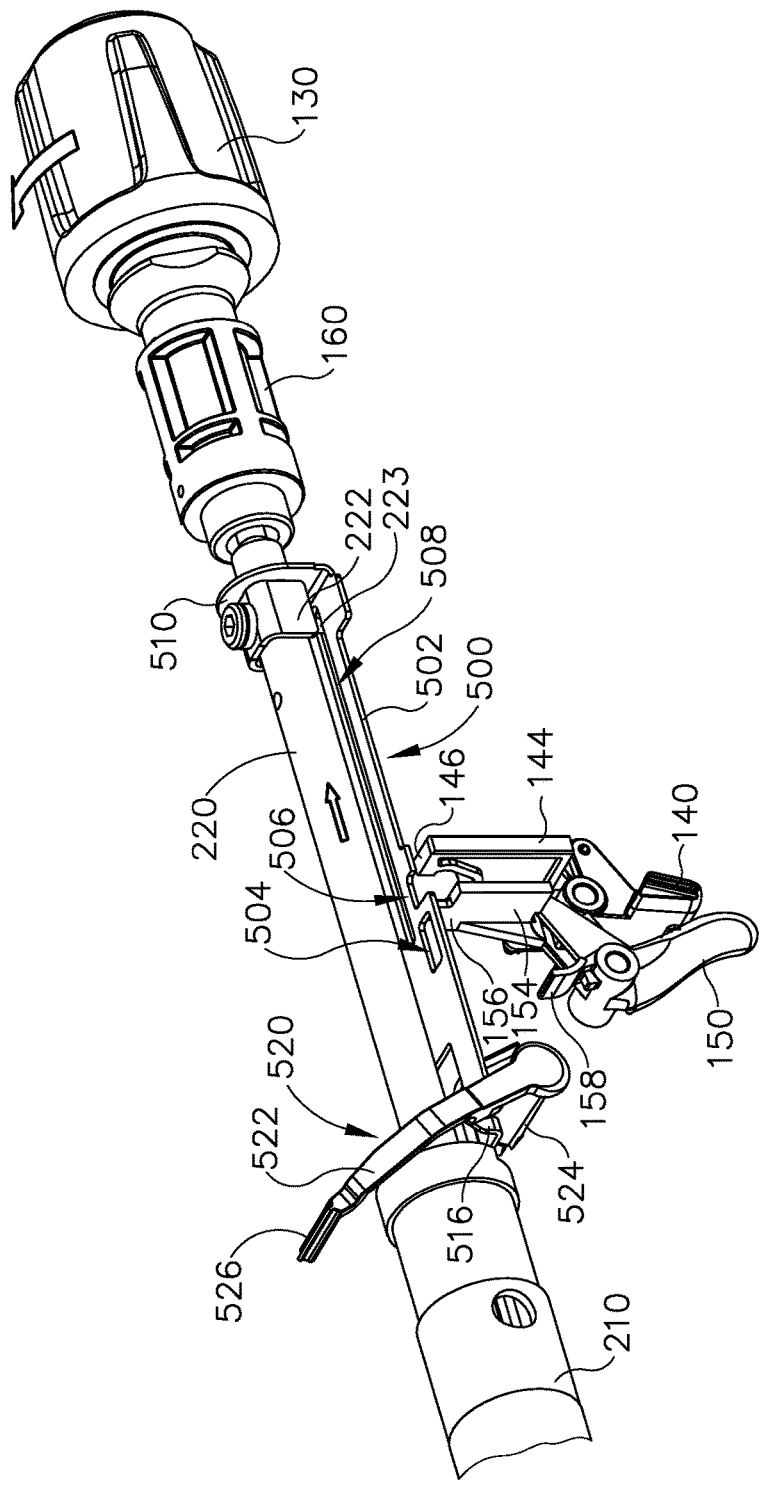
FIG. 12B depicts a perspective view of the anvil actuation assembly of FIG. 12A, with the actuation rod moved to a second position to engage the bracket of FIG. 10.
Figure 12C:
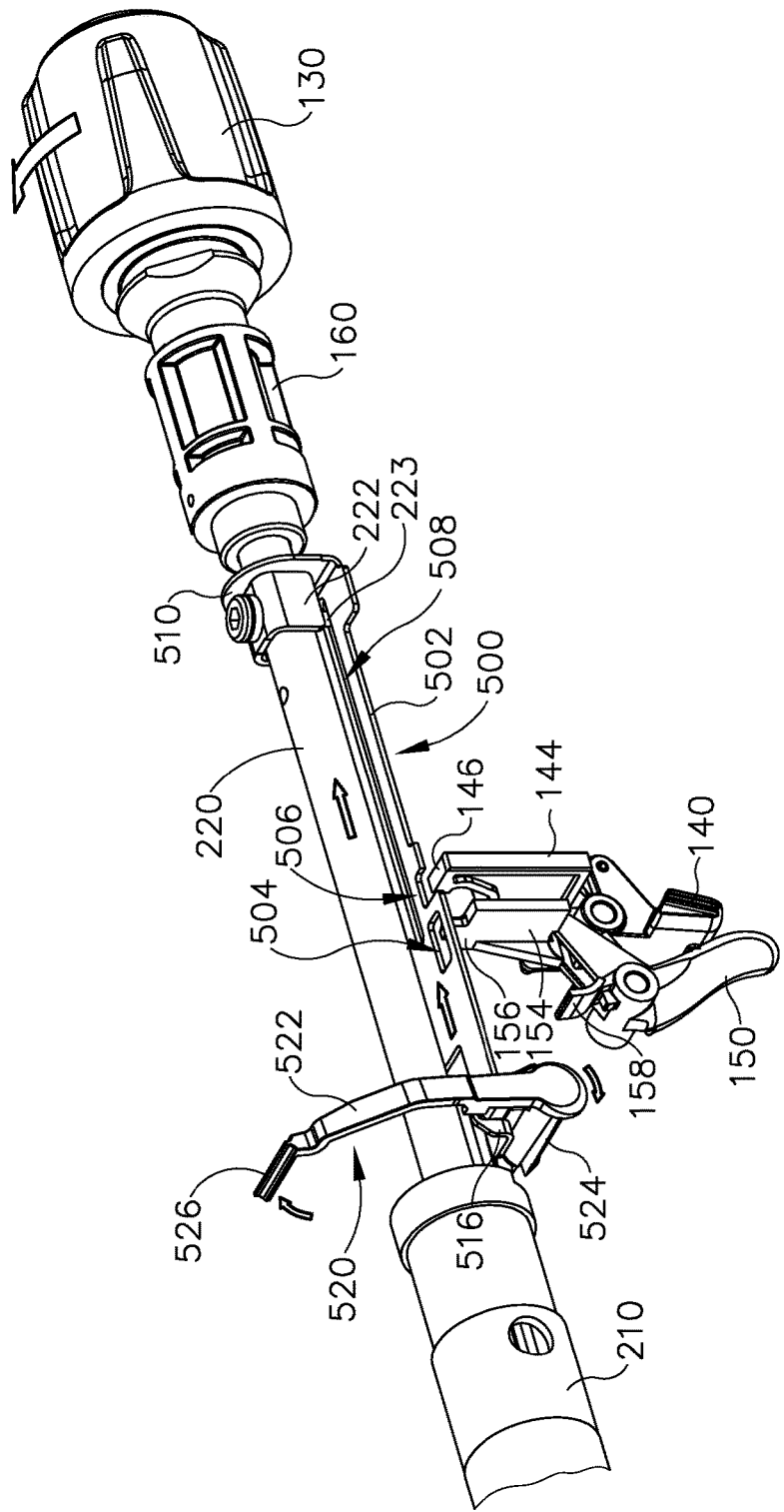
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotably coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
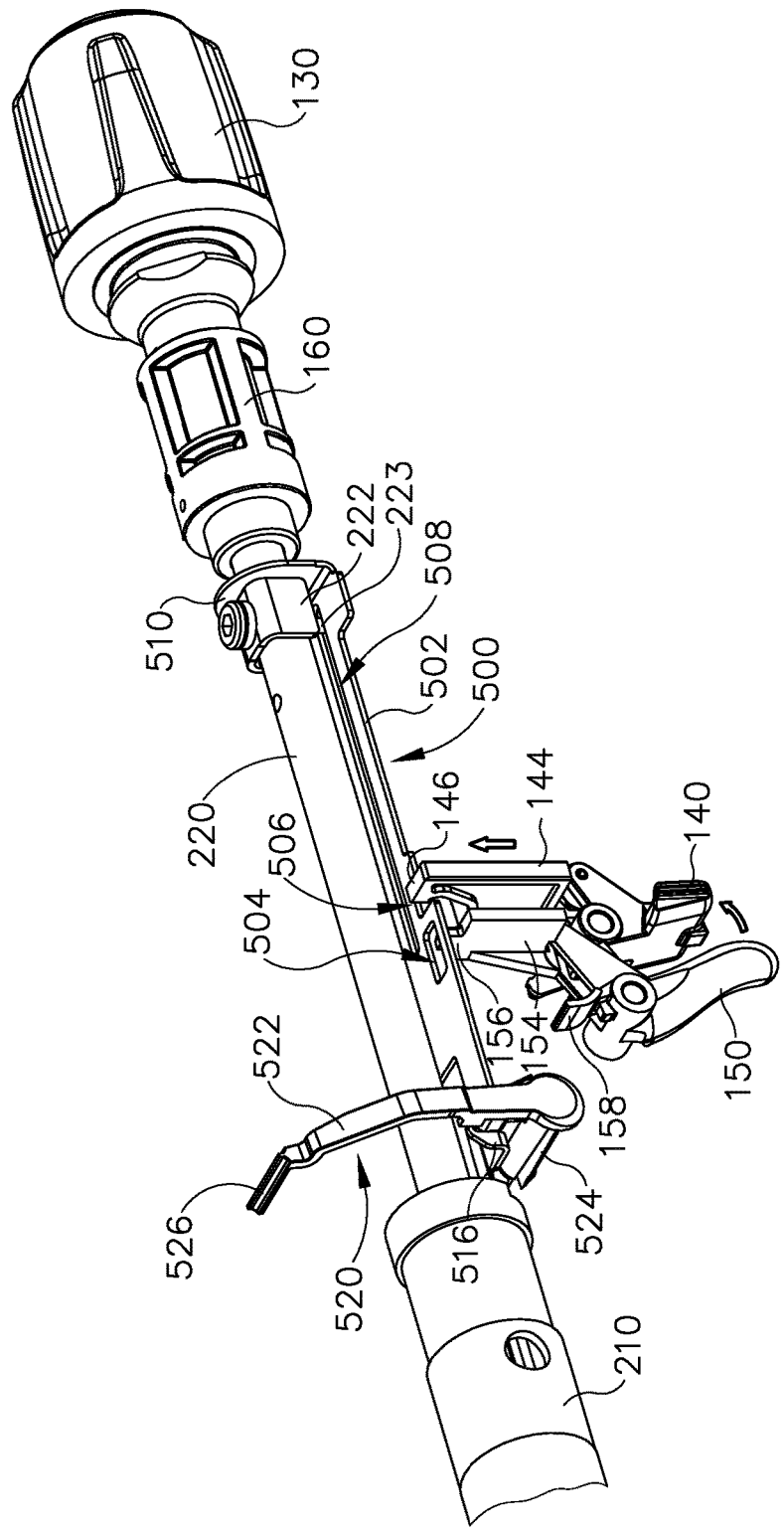
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
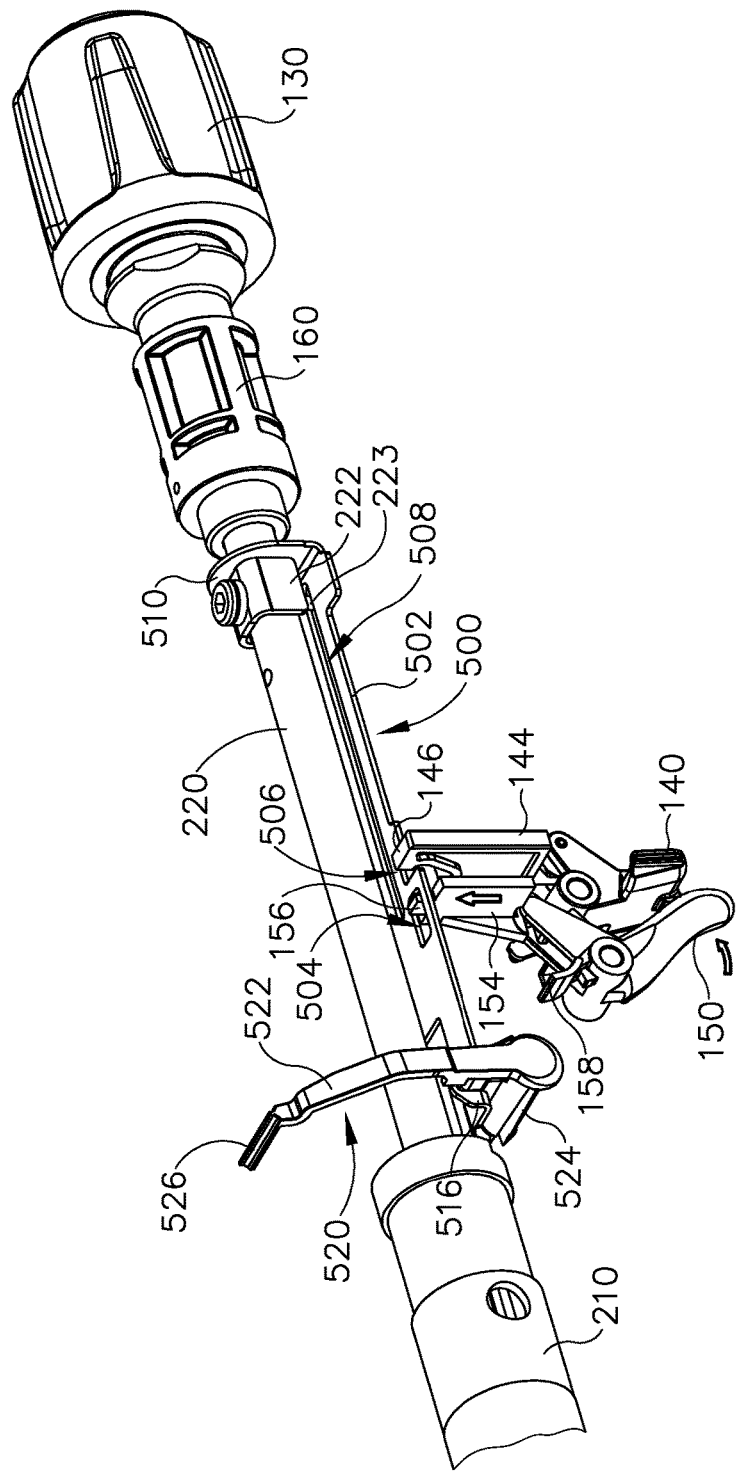
FIG. 12E depicts a perspective view of the anvil actuation assembly of FIG. 12A, with a firing trigger pivoted from a first position to a second position.
Figure 13:
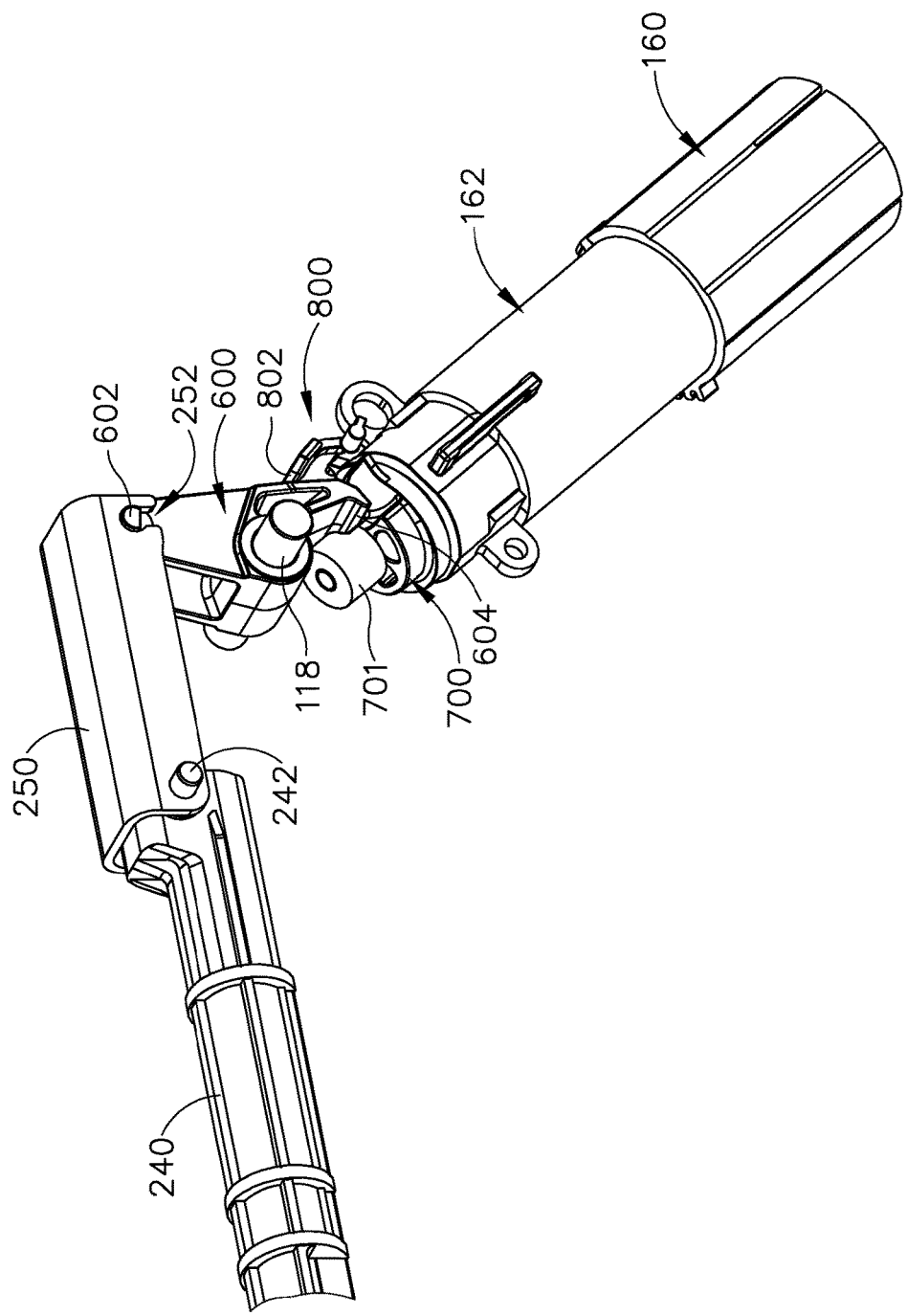
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
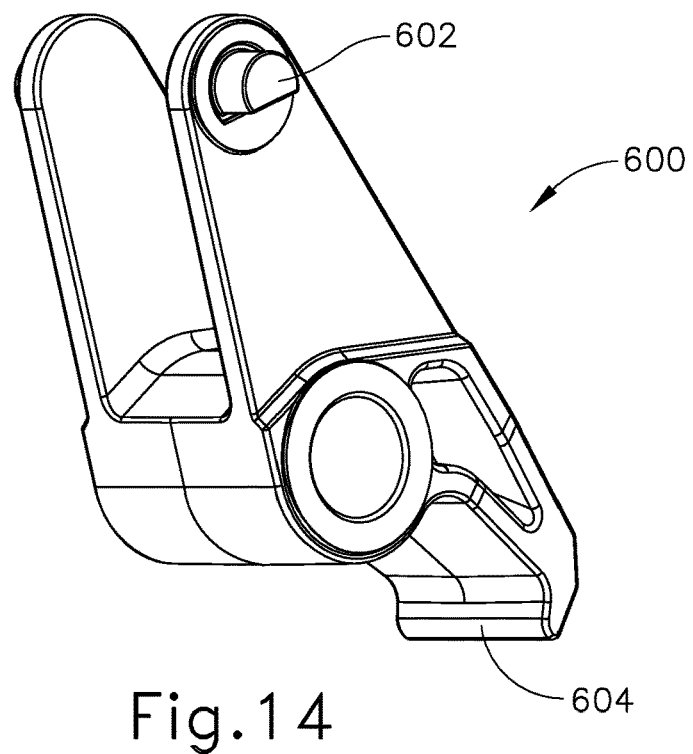
FIG. 14 depicts a perspective view of a cam follower of the stapling head actuation assembly of FIG. 13.
Figure 15:
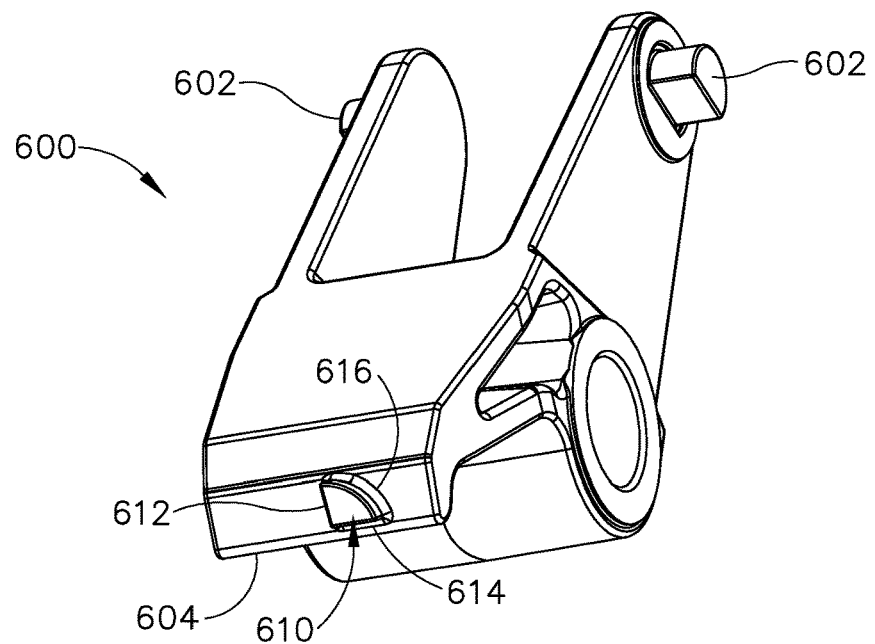
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
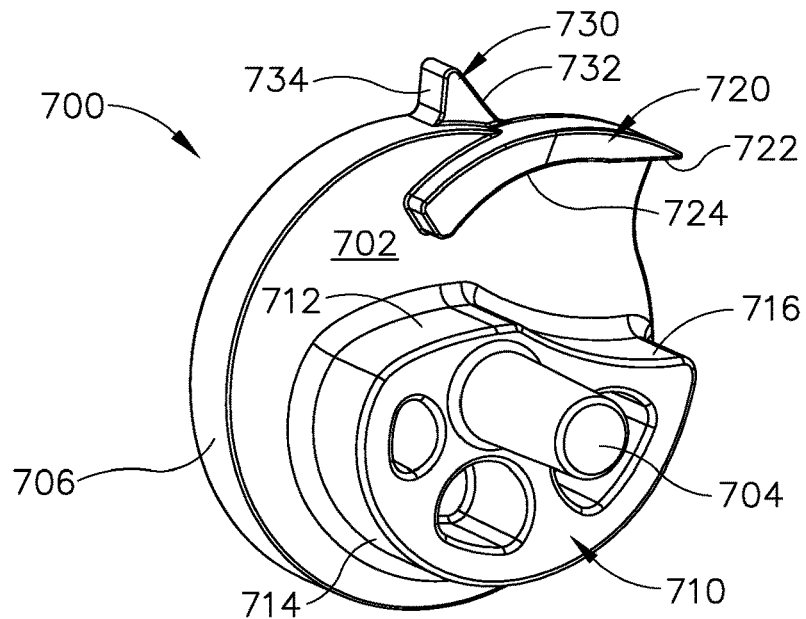
FIG. 16 depicts a perspective view of a rotary cam of the stapling head actuation assembly of FIG. 13.
Figure 17:
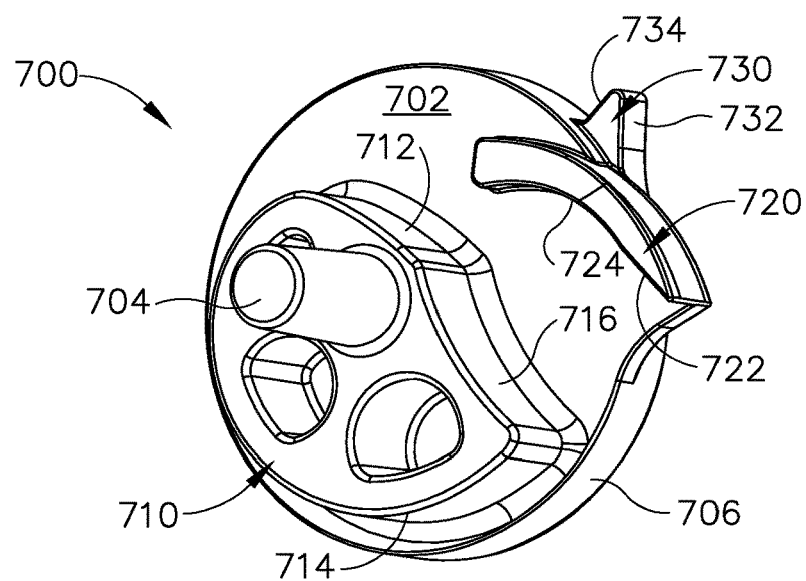
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
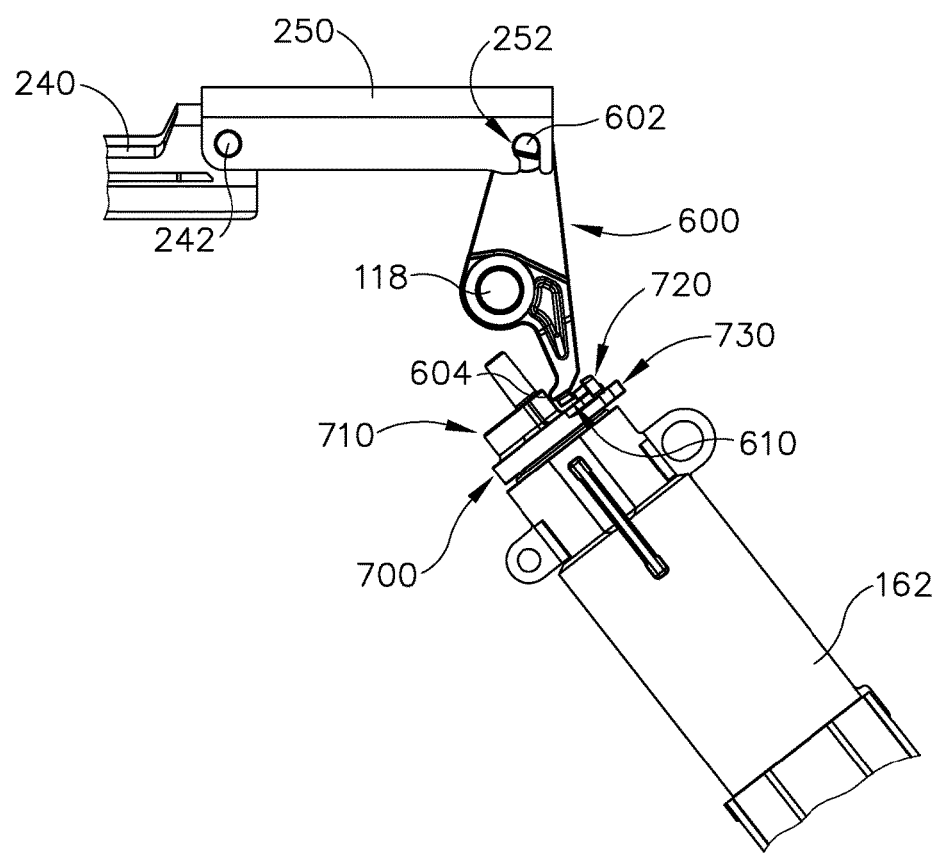
FIG. 18A depicts a side elevational view of the stapling head actuation assembly of FIG. 13, with the rotary cam in a first angular position and the cam follower in a first pivotal position.
Figure 18B:
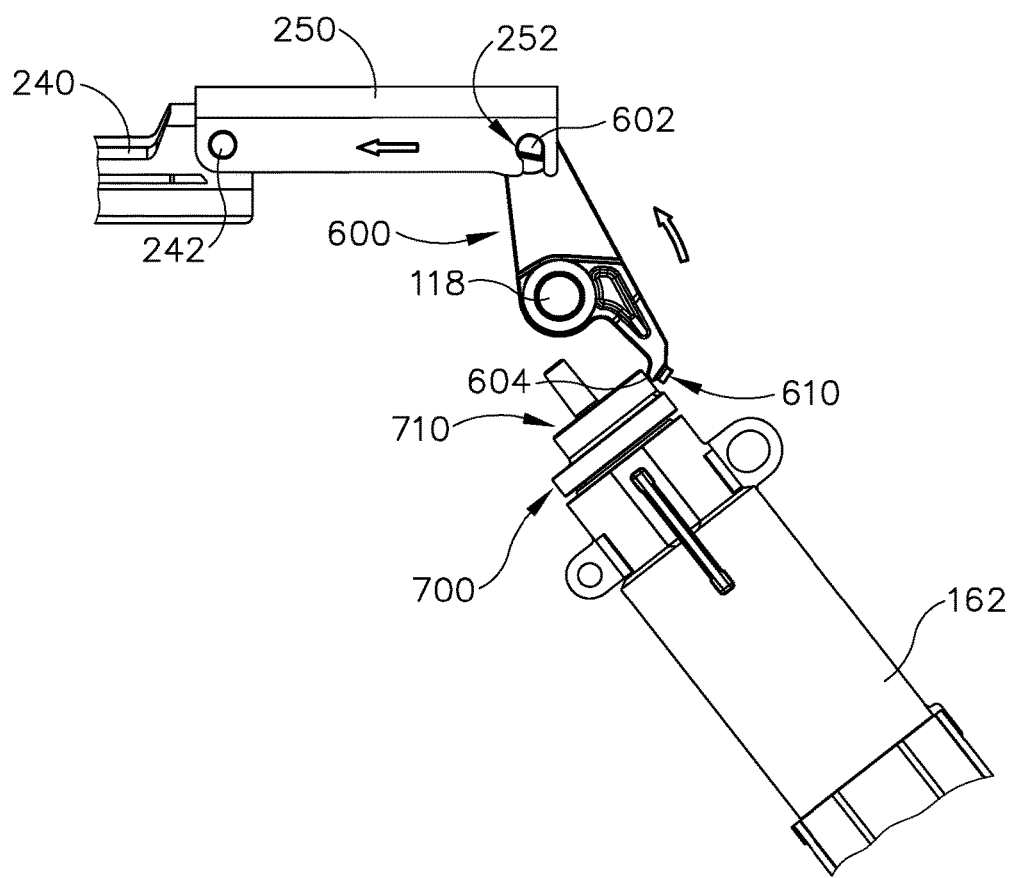
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
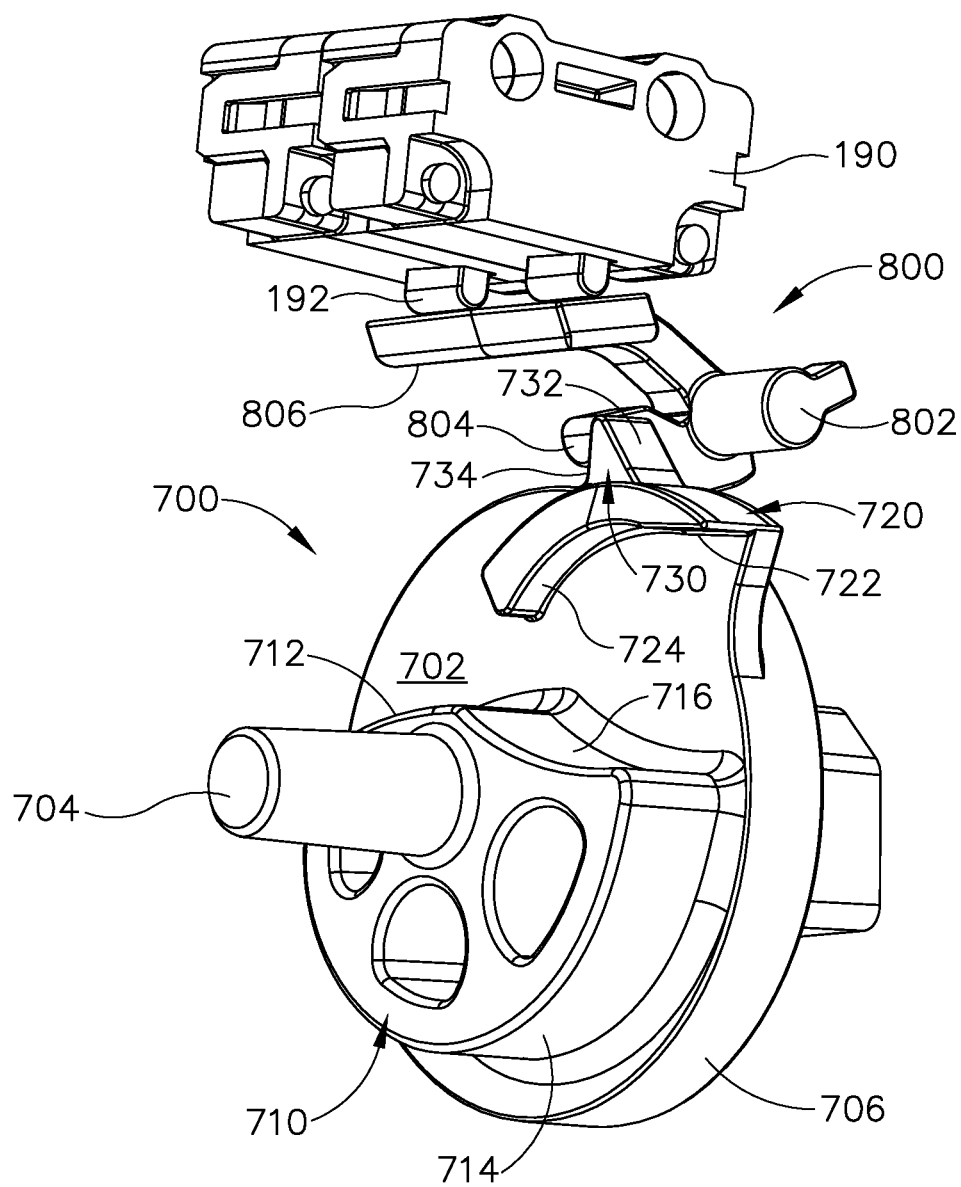
FIG. 19A depicts a perspective view of the rotary cam of FIG. 16, a rocker member, and a stop switch, with the rotary cam in a first angular position and the rocker member in a first pivotal position.
Figure 19B:
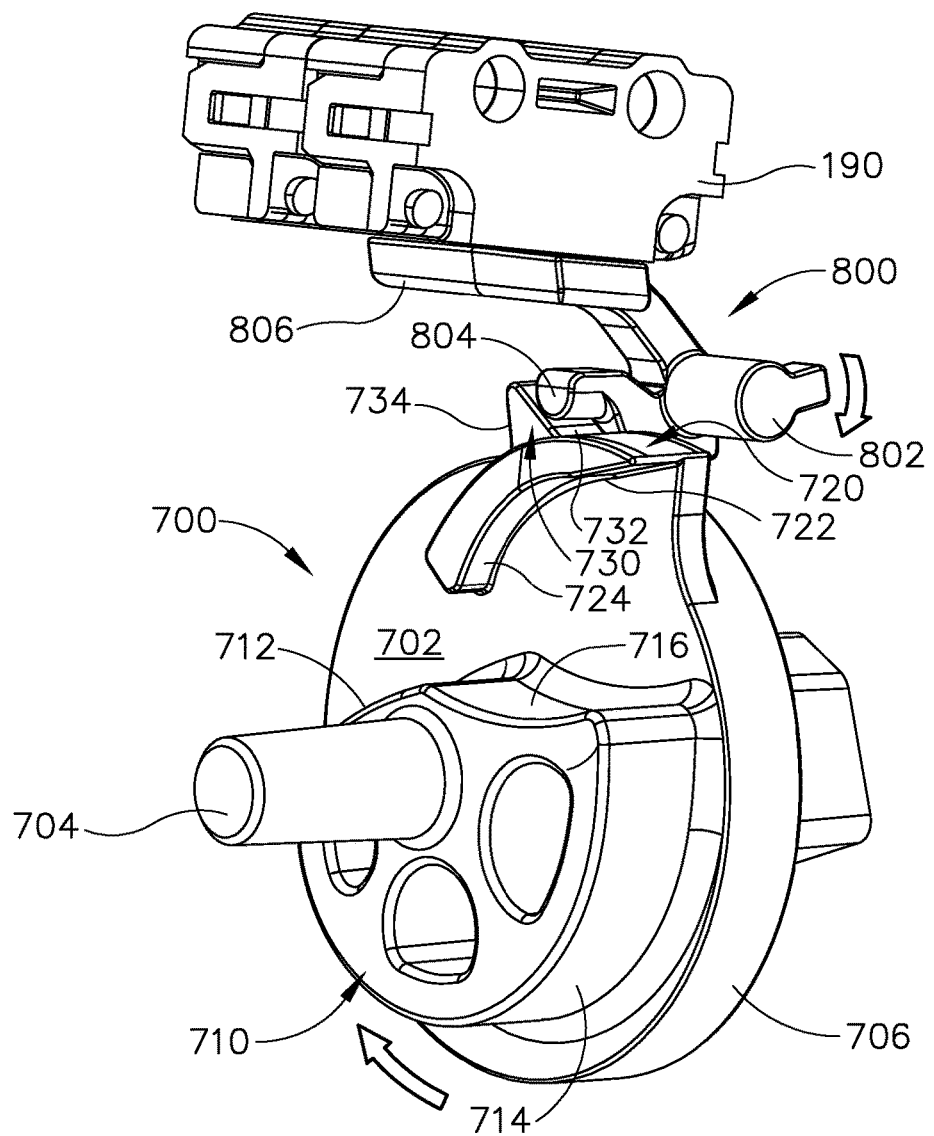
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160 once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

Figure 20A:
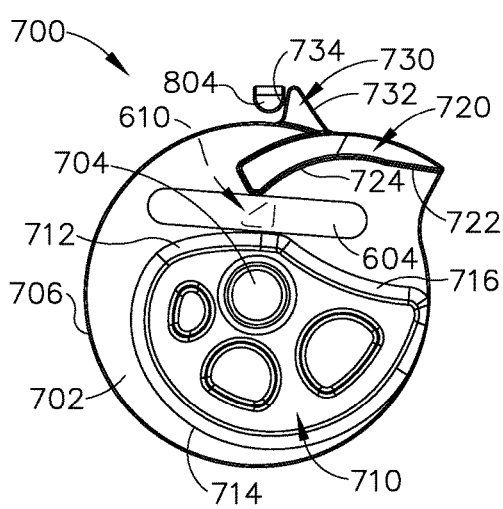
FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position.
Figure 20B:
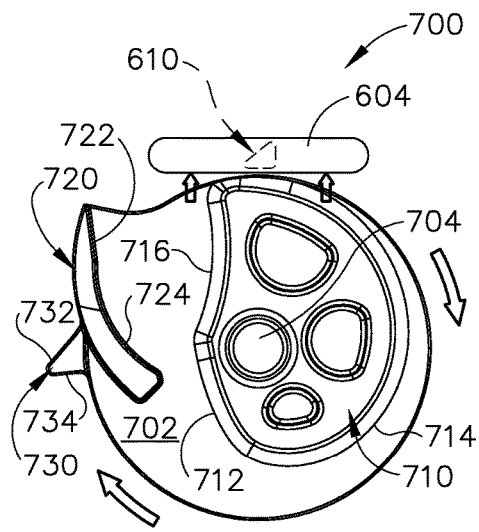
FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

Figure 20C:
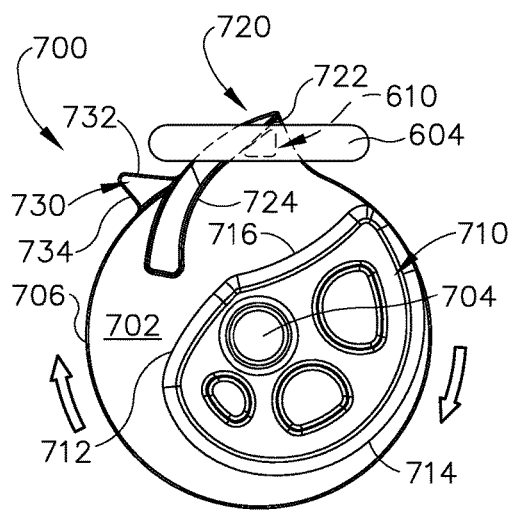
FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position.
Figure 20D:
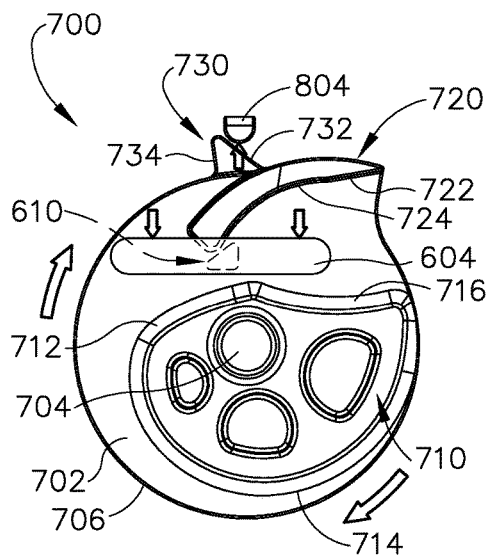
FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
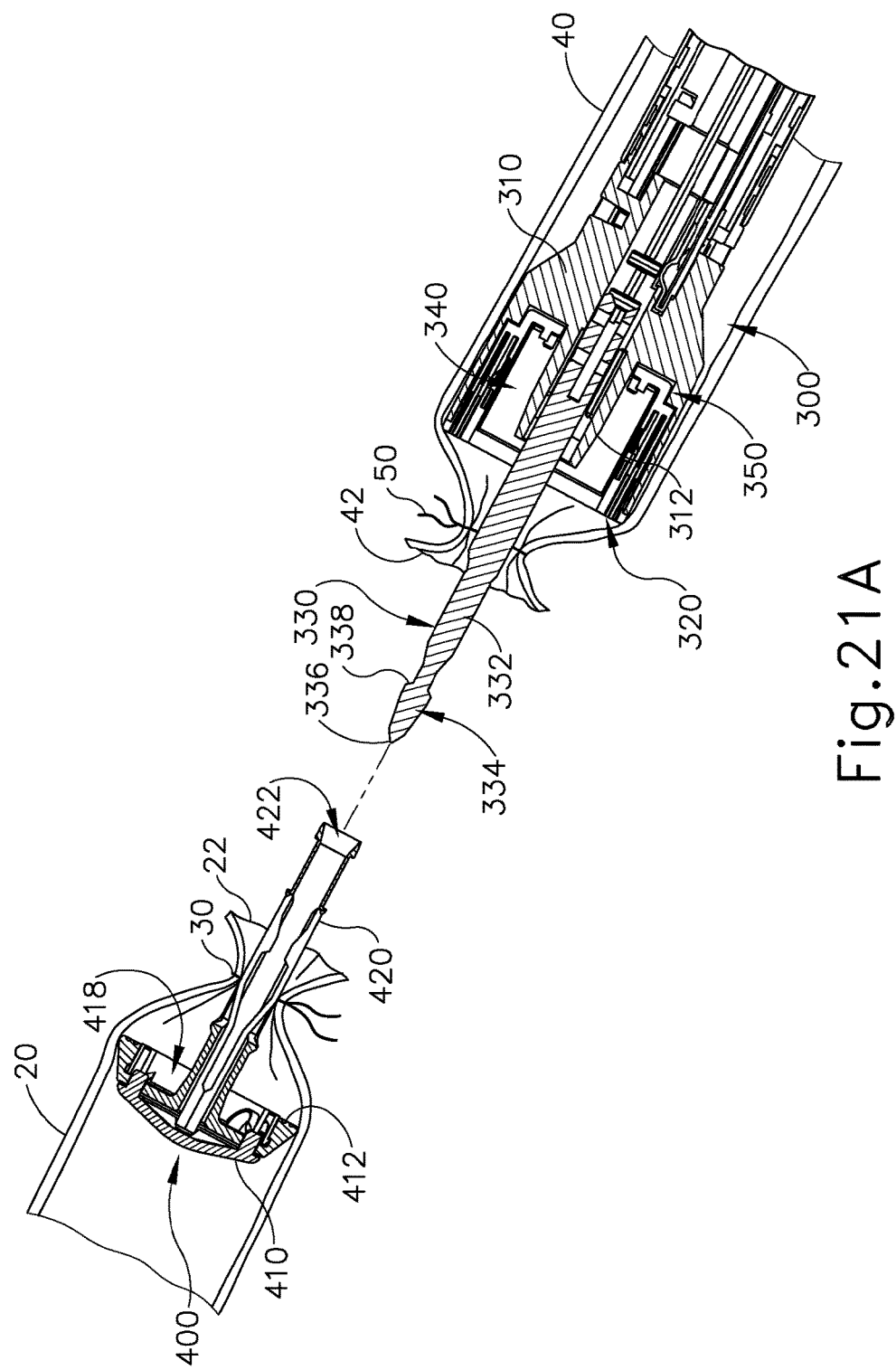
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
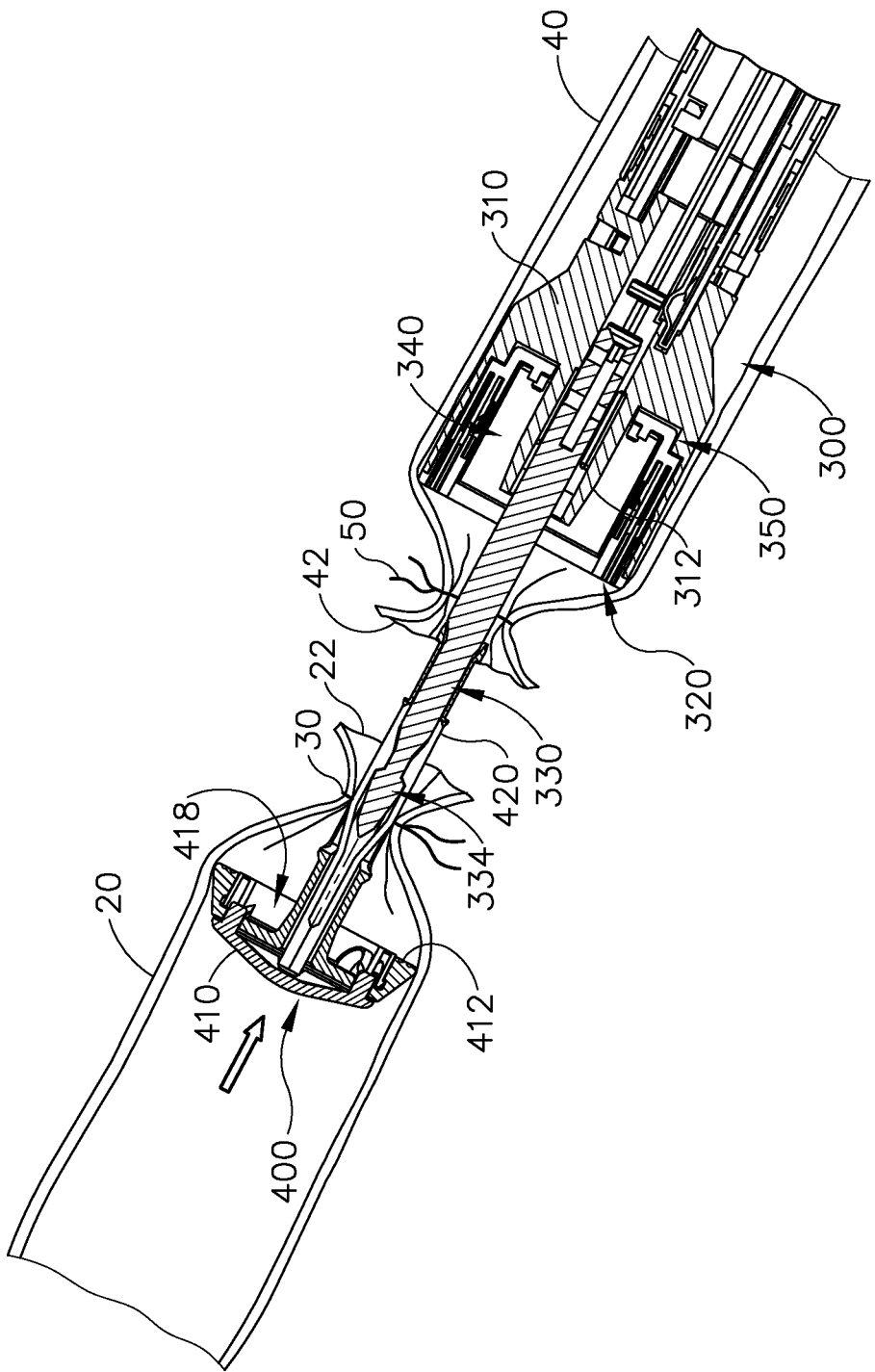
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
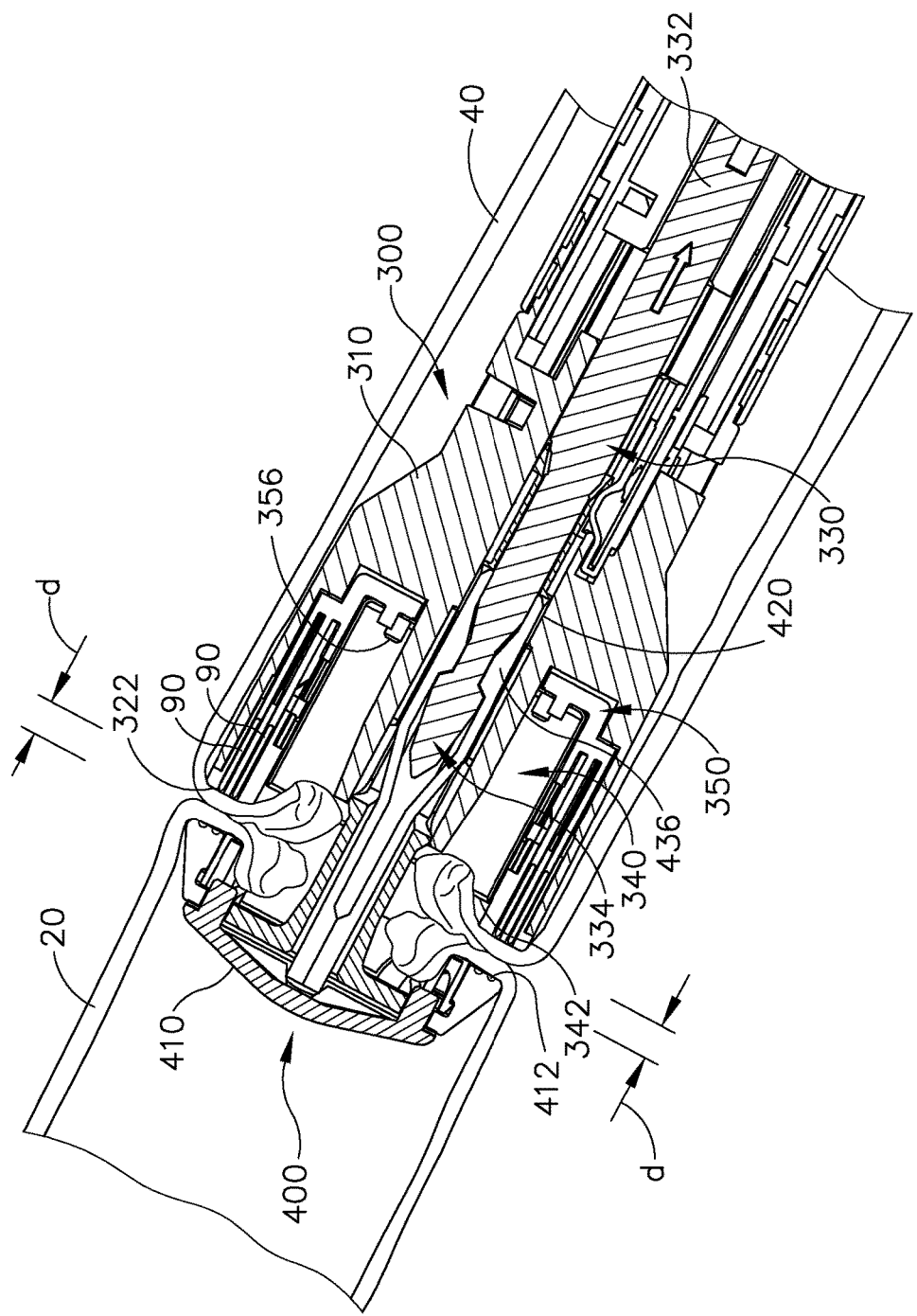
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Figure 21D:
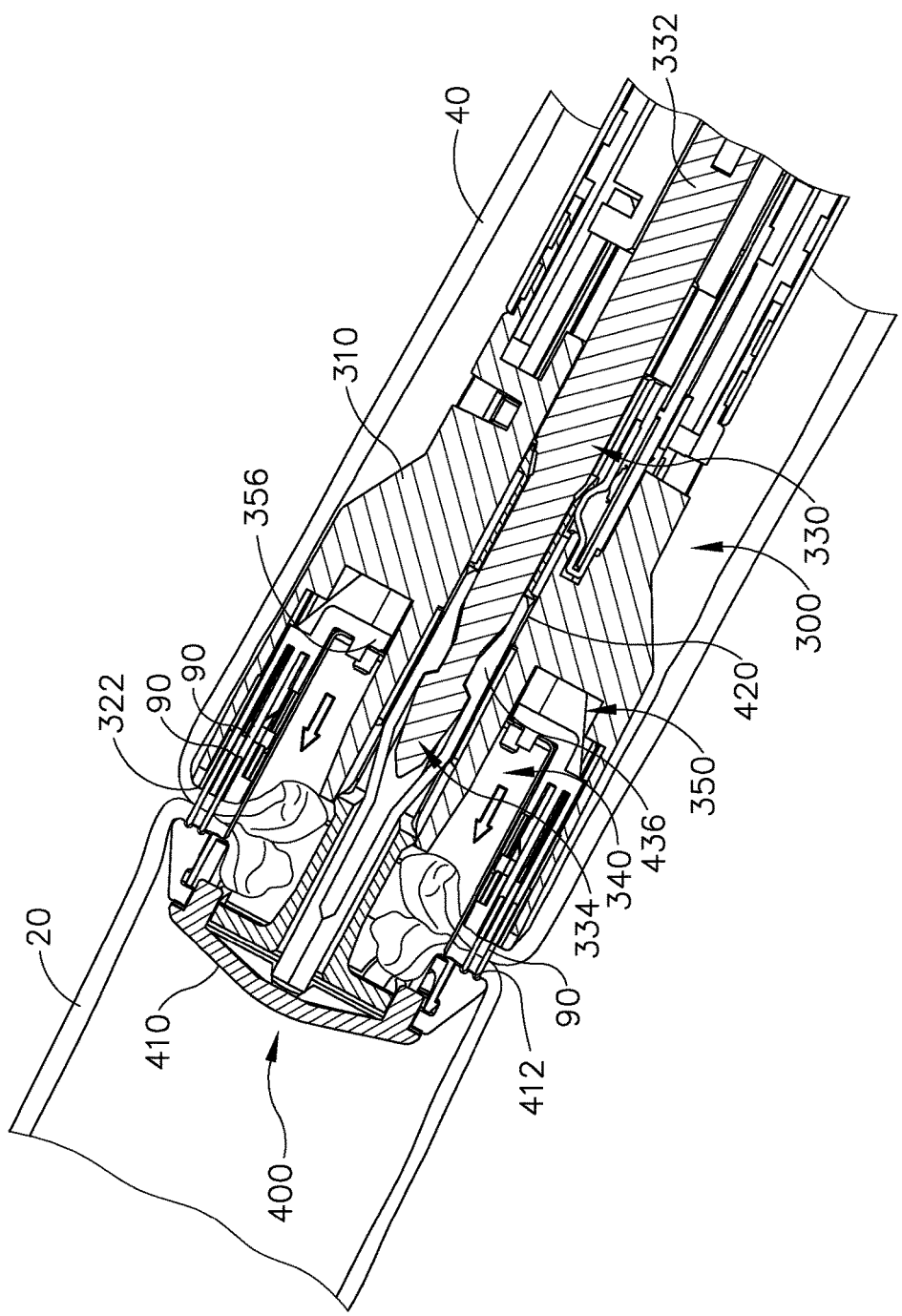
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS. 20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21E:
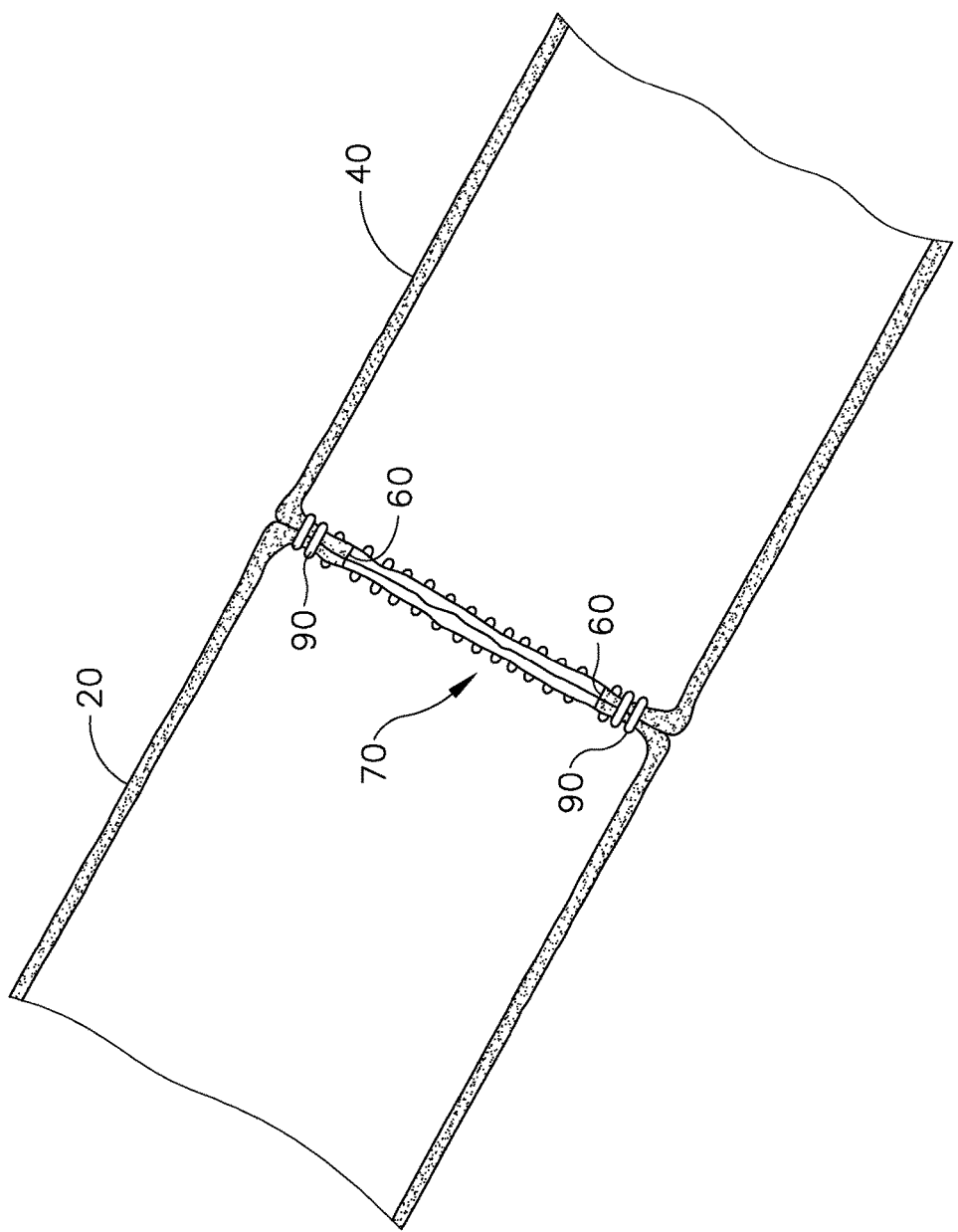
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Routines For Surgical Stapler

Figure 22A:
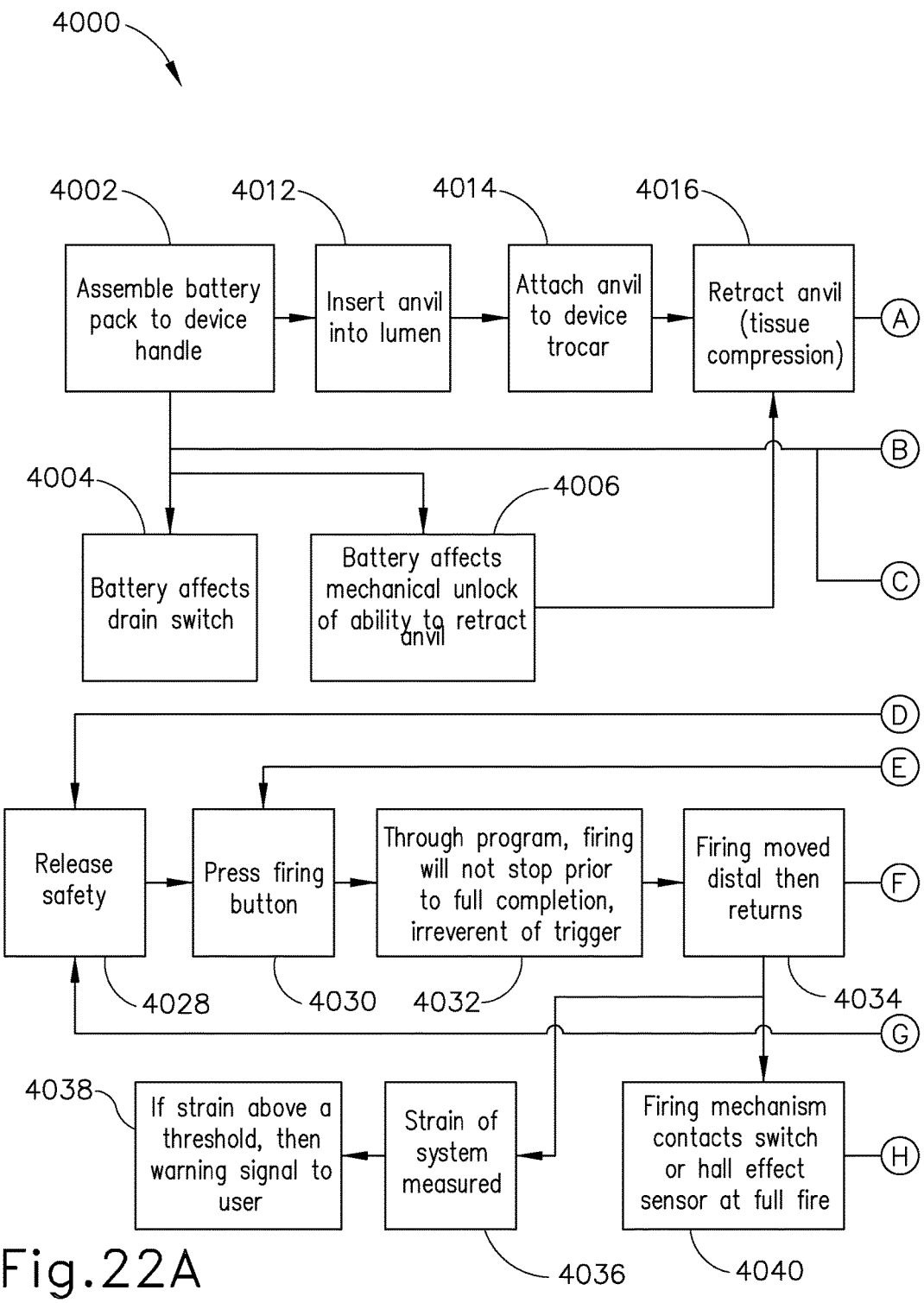
FIGS. 22A-22B depict a flow chart showing exemplary steps of operating the circular stapler of FIG. 1.
Figure 22B:
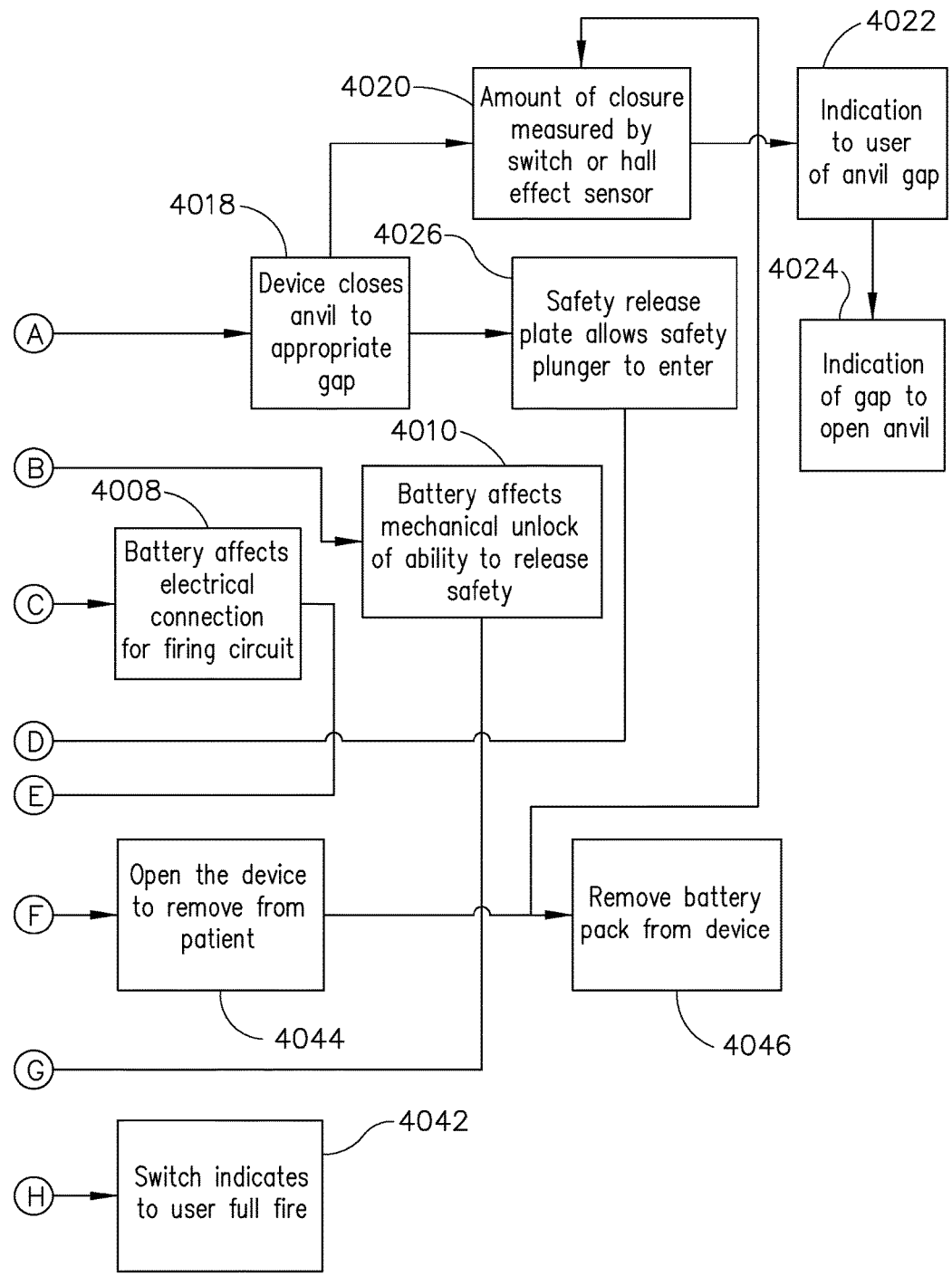

While the sequence described above with reference to FIGS. 21A-21E relate to how instrument (10) may be used by an operator in a surgical procedure, it should be understood that there are various routines that may be performed within instrument (10) before, during, and after the procedure depicted in FIGS. 21A-21E. FIGS. 22A-22B show various steps in an exemplary process (4000) that may be carried out through instrument (10) before, during, and after the procedure depicted in FIGS. 21A-21E. It should be understood that various steps of process (4000) are merely optional and may be omitted if desired.

In the present example, process (4000) begins with an operator inserting battery pack (120) into socket (116) of handle assembly (100), as shown in block (4002). In some versions, the insertion of battery back (120) into socket (116) will automatically trigger one or more additional steps in process (4000). For instance, as shown in block (4004), the insertion of battery back (120) into socket (116) may automatically activate a drain switch that begins to drain power from battery pack (120). By way of example only, such automatic drainage of power from battery pack (120) may be provided in accordance with at least some of the teachings of U.S. patent application Ser. No., entitled "Surgical Stapler with Ready State Indicator," filed on even date herewith, issued as U.S. Pat. No. 10,194,911 on Feb. 5, 2019, the disclosure of which is incorporated by reference herein. In addition or in the alternative, automatic drainage of power from battery pack (120) may be provided in accordance with at least some of the teachings below with reference to FIGS. 23A-23F. Other suitable ways in which power may be automatically drained from battery pack (120) upon insertion of battery back (120) into socket (116) will be apparent to those of ordinary skill in the art in view of the teachings herein. Alternatively, in some versions the step shown in block (4004) is simply omitted.

In addition to or as an alternative to automatically initiating drainage of power from battery pack (120), the insertion of battery pack (120) into socket (116) may also mechanically unlock the ability to retract trocar (330) and anvil (400) proximally, as shown in block (4006). By way of example only, such unlocking of the ability to retract trocar (330) and anvil (400) proximally may be provided in accordance with at least some of the teachings of U.S. Patent App. No. , entitled "Surgical Stapler with Ready State Indicator," filed on even date herewith, issued as U.S. Pat. No. 10,194, 991 on Feb. 5, 2019, the disclosure of which is incorporated by reference herein. Other suitable ways in which the ability to retract trocar (330) and anvil (400) proximally may be automatically unlocked upon insertion of battery back (120) into socket (116) will be apparent to those of ordinary skill in the art in view of the teachings herein. Alternatively, in some versions the step shown in block (4006) is simply omitted.

It should also be understood that the insertion of battery pack (120) into socket (116) may provide a necessary electrical connection within the circuit that actuates stapling head assembly (300), as shown in block (4008). In other words, in the absence of battery pack (120), the circuit that actuates stapling head assembly will lack a necessary electrical connection. In some other versions, instrument (10) is capable of receiving electrical power from some other source, such that battery pack (120) need not necessarily be inserted into socket (116) in order to complete a circuit that is operable to actuate stapling head assembly (300).

In some versions, the insertion of battery pack (120) into socket (116) may also mechanically unlock the ability to actuate safety trigger (140), as shown in block (4010). Various suitable ways in which the insertion of battery pack (120) into socket (116) may mechanically unlock the ability to actuate safety trigger (140) will be apparent to those of ordinary skill in the art in view of the teachings herein. Alternatively, in some versions the step shown in block (4010) is simply omitted.

Regardless of whether (or the extent to which) the steps shown in blocks (4004, 4006, 4008, 4010) are ultimately included in process (4000), process (400) may proceed with insertion of anvil (400) into anatomical structure (20), as shown in block (4012). This step is also shown in FIG. 21A as discussed above. Continuing on with process (4000) as shown in FIGS. 22A-22B, anvil (400) is then secured to trocar (330) as shown in block (4014). This step is also shown in FIG. 21B as discussed above. Continuing on with process (4000) as shown in FIGS. 22A-22B, anvil (400) and trocar (330) are then retracted proximally to compress the tissue of anatomical structures (20, 40), as shown in block (4016). This step is also shown in FIG. 21C as discussed above. The operator rotates knob (130) in order to achieve an appropriate gap distance (d), as shown in block (4018). This step is also shown in FIGS. 12B-12C and 21C as discussed above.

In some instances, instrument (10) includes electromechanical features that monitor the gap distance (d) and provide feedback to the operator relating to the gap distance (d). By way of example only, such features may be provided in accordance with at least some of the teachings of U.S. Patent App. No. , entitled "Surgical Stapler with Ready State Indicator," filed on even date herewith, issued as U.S. Pat. No. 10,194,911 on Feb. 5, 2019, the disclosure of which is incorporated by reference herein. Other suitable ways in which an instrument (10) may monitor the gap distance (d) and provide feedback to the operator relating to the gap distance (d) will be apparent to those of ordinary skill in the art in view of the teachings herein. For those versions of instrument (10) that do have this capability, process (4000) includes such monitoring of the gap distance (d) as shown in block (4020). Instrument (10) may provide audible, visual, and or tactile feedback relating to the gap distance (d) as shown in block (4022). In the event that the gap distance (d) falls below the clinically acceptable range (i.e., anvil (400) is getting too close to stapling head assembly (300)), instrument (10) my provide an indication to the operator to indicate that anvil (400) needs to be advanced distally to increase the gap distance (d), as shown in block (4024).

Regardless of whether instrument (10) includes electromechanical features that monitor the gap distance (d) and provide feedback to the operator relating to the gap distance (d), bracket (500) will move to a position where it unblocks actuation of safety trigger (140) when the gap distance (d) reaches the clinically acceptable range, as shown in block (4026). Such positioning of bracket (500) is also shown in FIG. 12C as described above. The operator may actuate safety trigger (140) once bracket (500) has moved into the unblocking position, as shown in block (4028). Such actuation of safety trigger (140) is also shown in FIG. 12D as described above. Once safety trigger (130) has been actuated, the operator may then actuate firing trigger (150), as shown in block (4030). Such actuation of firing trigger (150) is also shown in FIG. 12E as described above.

Once the operator actuates firing trigger (150), instrument (10) will complete an actuation stroke of stapling head assembly (300), regardless of what the operator does next with firing trigger (150), as shown in block (4032). In other words, the assembly that actuates stapling head assembly (300) (i.e., motor (160) and the rest of the components that couple motor (160) with stapling head assembly (300)) will effectively be fully committed to actuating stapling head assembly (300) once the operator actuates firing trigger (150), even if the operator further manipulates firing trigger (150). By way of example only, instrument (10) may include components that provide full commitment to the actuation of stapling head assembly (300) in response to actuation of firing trigger (150) in accordance with at least some of the teachings of U.S. Pub. No. 2015/0083774, entitled "Control Features for Motorized Surgical Stapling Instrument," published Mar. 26, 2015, issued as U.S. Pat. No. 9,907,552 on Mar. 6, 2018, the disclosure of which is incorporated by reference herein. Alternatively, instrument (10) may include components that provide full commitment to the actuation of stapling head assembly (300) in response to actuation of firing trigger (150) in accordance with the teachings below.

The actuation stroke of stapling head assembly (300) includes the distal and proximal motion of various components, as shown in block (4034). This alternating motion is shown in FIGS. 18A-18B and in FIGS. 20A-20D as described above. The distal motion is also shown in FIG. 21D as described above.

In some versions of instrument (10), while the firing mechanism completes the actuation stroke of stapling head assembly (300), instrument (10) may include features that detect strain within the firing mechanism as shown in block (4036). By way of example only, such sensing may be provided in accordance with at least some of the teachings of U.S. patent application Ser. No. 14/751,406, entitled "Surgical Stapler with Incomplete Firing Indicator," filed on even date herewith, issued as U.S. Pat. No. 10,265,066 on Apr. 23, 2019, the disclosure of which is incorporated by reference herein. Other suitable ways in which instrument (10) may incorporate features that sense strain in the firing system be apparent to those of ordinary skill in the art in view of the teachings herein. Alternatively, such features may be omitted such that the step shown in block (4036) is omitted. In the event that such features are included, instrument (10) may provide an audible, visual, and/or tactile indication in the event that the sensing feature(s) detected that the strain has exceeded a threshold, as shown in block (4038).

In addition to or as an alternative to features that detect strain in the firing mechanism during the actuation stroke of stapling head assembly (300), some versions of instrument (10) may include a switch or other kind of sensor that detects whether a portion of the firing mechanism has traveled to an expected distance during the actuation stroke, as indicated in block (4040). By way of example only, such sensing may be provided in accordance with at least some of the teachings of U.S. Pat. App. No., entitled "Surgical Stapler with Incomplete Firing Indicator," filed on even date herewith, issued as U.S. Pat. No. 10,265,066 on Apr. 23, 2019, the disclosure of which is incorporated by reference herein. Other suitable ways in which instrument (10) may incorporate features that sense whether the firing mechanism has completed sufficient travel will be apparent to those of ordinary skill in the art in view of the teachings herein. Alternatively, such features may be omitted such that the step shown in block (4040) is omitted. In the event that such features are included, instrument (10) may provide an audible, visual, and/or tactile indication in the event that the sensing feature(s) detected that the actuation stroke of stapling head assembly (300) was successfully completed, as shown in block (4042).

Once stapling head assembly (300) has been successfully actuated, anvil (400) may be advanced distally from stapling head assembly (300) and instrument (10) may be withdrawn from the patient, as shown in block (4044). After instrument (10) has been withdrawn from the patient, the operator may remove battery pack (120) from handle assembly (100), as shown in block (4046).

As noted above, the above-described steps of process (4000) are merely illustrative examples. Instrument (10) may be used in various other ways as will be apparent to those of ordinary skill in the art in view of the teachings herein. In addition, instrument (10) may have various other functionalities as will be apparent to those of ordinary skill in the art in view of the teachings herein.

III. Exemplary Control Circuits For Surgical Stapler

As noted above with reference to block (4032), it may be desirable to ensure that the firing mechanism for stapling head assembly (300) completes a full actuation stroke in response to actuation of firing trigger (150). In other words, it may be desirable to prevent subsequent manipulation of firing trigger (150) from having any effect on the firing mechanism completing the actuation stroke of stapling head assembly (300). In some instances, instrument (10) may incorporate mechanical features that ensure completion of a full actuation stroke of stapling head assembly (300) in response to actuation of firing trigger (150), regardless of subsequent manipulation of firing trigger (150). Examples of such mechanical features are described in U.S. Pub. No. 2015/0083774, entitled "Control Features for Motorized Surgical Stapling Instrument," published Mar. 26, 2015, issued as U.S. Pat. No. 9,907,552 on Mar. 6, 2018, the disclosure of which is incorporated by reference herein. In addition to or as a alternative to using such mechanical features, instrument (10) may include electronic components that ensure completion of a full actuation stroke of stapling head assembly (300) in response to actuation of firing trigger (150), regardless of subsequent manipulation of firing trigger (150). Several examples of such electrical features are described in greater detail below, while further examples will be apparent to those of ordinary skill in the art in view of the teachings herein.

A. Exemplary Relay-Based Control Circuit for Surgical Stapler

FIGS. 23A-23F show an exemplary circuit (4100) that may be readily incorporated into instrument (10). In particular, circuit (4100) includes components that may be incorporated into motor activation module (180) and short circuit module (190). Circuit (4100) further includes battery pack (120), motor (160), a battery drain module (4112), and a feedback module (4130).

In the present example, motor activation module (180) includes a switch (4120) and a relay (4122). Switch (4120) is configured to be closed by paddle (158) of firing trigger (150) when firing trigger (150) is pivoted from the position shown in FIG. 12D to the position shown in FIG. 12E. By way of example only, switch (4120) may comprise a single pole single throw (SPST) momentary tactile switch. Alternatively, switch (4120) may take any other suitable form. Relay (4122) comprises a conventional polarized double pole double throw (DPDT) relay, such that relay (4122) includes a pair of integral switches (4124). Motor activation module (180) is in communication with motor (160) and battery pack (120) via feedback module (4130).

Short circuit module (190) of the present example comprises a pair of switches (4140). Switches (4140) are configured to be actuated by paddle (806) of rocker member (800) when rocker member is pivoted from the position shown in FIGS. 19A and 20A-20C to the position shown in FIGS. 19B and 20D. Short circuit module (190) is in communication with motor (160) and motor activation module (4120) via feedback module (4130).

Battery drain module (4112) of the present example comprises a pair of resistors and a positive temperature coefficient (PTC) current limiting device. By way of example only, battery drain module (4112) may be constructed and operable in accordance with at least some of the teachings of U.S. Patent app. No., entitled "Surgical Stapler with Ready State Indicator," filed on even date herewith, issued as U.S. Pat. No. 10,194,991 on Feb. 5, 2019, the disclosure of which is incorporated by reference herein. Battery drain module (4112) is in communication with a switch (4110), with battery (120), and with feedback module (4130).

Feedback module (4130) of the present example comprises a pair of backlight light emitting diodes (LEDs) (4132) and an indicator LED (4134). Backlight LEDs (4132) are configured and positioned to provide backlight illumination to a display that is provided in window (114). As noted above, window (114) is operable to reveal the position of indicator needle (526) as the operator adjusts the gap distance (d) between opposing surfaces (412, 322) of anvil (400) and stapling head assembly (300). Backlight LEDs (4132) may thus assist in visualization of the position of indicator needle (526) in window (114). In addition or in the alternative, window (114) may include a backlit display that is configured and operable in accordance with at least some of the teachings of U.S. Patent App. No., entitled "Surgical Stapler with Ready State Indicator," filed on even date herewith, issued as U.S. Pat. No. 10,194,911 on Feb. 5, 2019, the disclosure of which is incorporated by reference herein. In addition or in the alternative, window (114) may include a backlit display that is configured and operable in accordance with at least some of the teachings of U.S. Patent App. No., entitled "Surgical Stapler with Anvil State Indicator," filed on even date herewith, issued as U.S. Pat. No. 10,188,386 on Jan. 29, 2019, the disclosure of which is incorporated by reference herein. Other suitable displays that may be provided through window (114) and backlit by LEDs (4132) will be apparent to those of ordinary skill in the art in view of the teachings herein. It should also be understood that backlight LEDs (4132) are merely optional and may be omitted if desired.

Indicator LED (4134) is configured to illuminate, change color, or otherwise react to an operational condition associated with instrument (10). For instance, indicator LED (4134) may be configured to provide visual feedback indicating whether anvil (400) is fully coupled with trocar (330). Indicator LED (4134) may thus be in communication with anvil (400) detection features such as those taught in U.S. Patent App. No., entitled "Surgical Stapler with Anvil Seating Detection," filed on even date herewith, issued as U.S. Pat. No. 10,307,157 on Jun. 4, 2019 the disclosure of which is incorporated by reference herein. In addition or in the alternative, indicator LED (4134) may be configured to provide visual feedback indicating whether stapling head assembly (300) is in a ready to fire state. Indicator LED (4134) may thus be in communication with anvil (400) features such as those taught in U.S. Patent App. No., entitled "Surgical Stapler with Ready State Indicator," filed on even date herewith, issued as U.S. Pat. No. 10,194,911 on Feb. 5, 2019, the disclosure of which is incorporated by reference herein. In addition or in the alternative, indicator LED (4134) may be configured to provide visual feedback indicating whether anvil (400) has been sufficiently advanced away from stapling head assembly (300) after a firing stapling head assembly (300) has been actuated and before instrument (10) is removed from the patient. Indicator LED (4134) may thus be in communication with anvil (400) position detection features such as those taught in U.S. Patent App. No., entitled "Surgical Stapler with Anvil State Indicator," filed on even date herewith, issued as U.S. Pat. No. 10,188,386 on Jan. 29, 2019, the disclosure of which is incorporated by reference herein. In addition or in the alternative, indicator LED (4134) may be configured to provide visual feedback indicating a level of stress within the firing mechanism for stapling head assembly (300) and/or indicating whether stapling head assembly (300) has been fully actuated. Indicator LED (4134) may thus be in communication with sensing components such as those taught in U.S. Patent App. No., entitled "Surgical Stapler with Incomplete Firing Indicator," filed on even date herewith, issued as U.S. Pat. No. 10,265,066 on Apr. 23, 2019, the disclosure of which is incorporated by reference herein. Still other conditions that may be indicated through indicator LED (4134) will be apparent to those of ordinary skill in the art in view of the teachings herein. It should also be understood that feedback module (4130) may include any suitable number of indicator LEDs (4134); or may simply lack an indicator LED (4134) altogether.

Figure 23A:
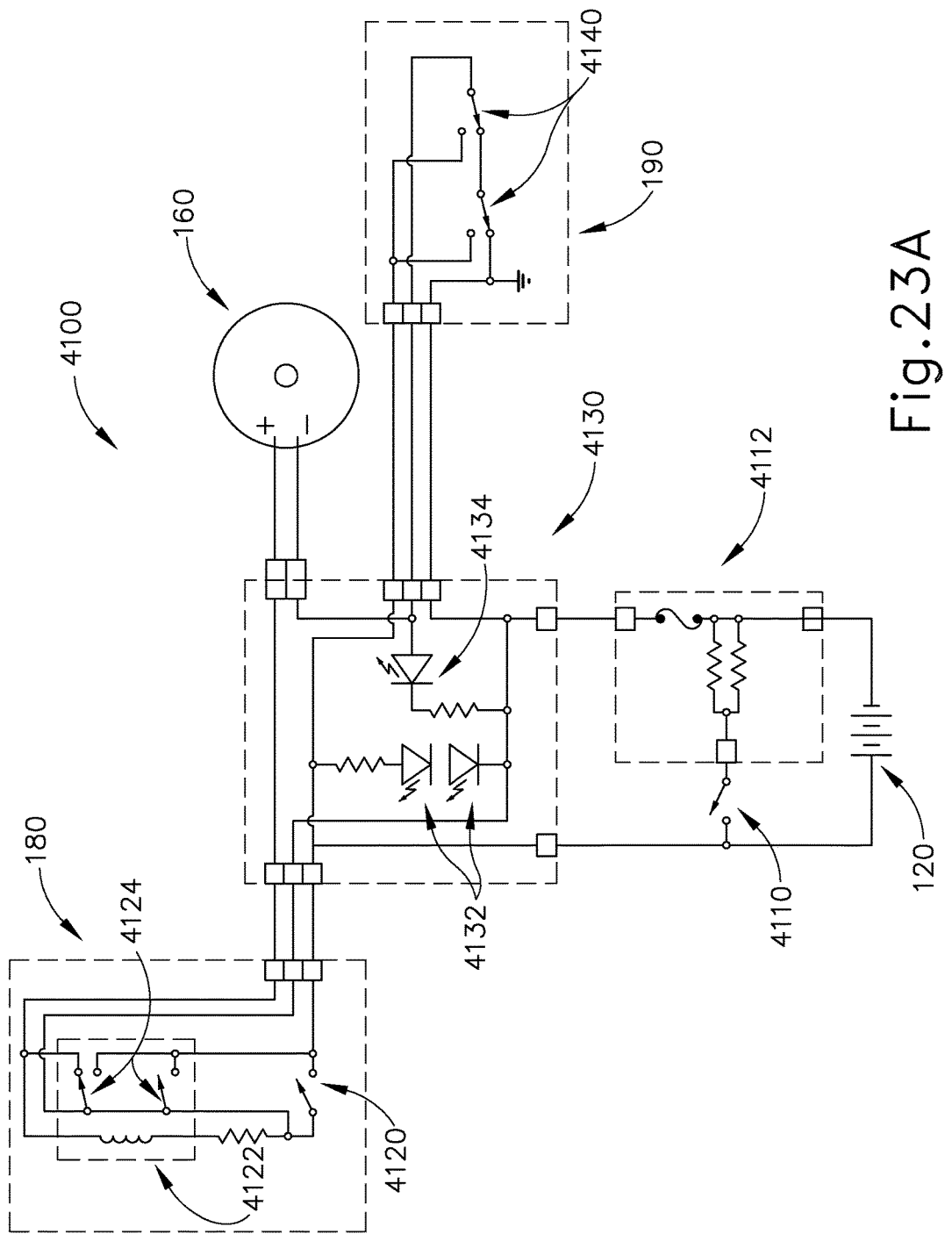
FIG. 23A depicts a schematic view of an exemplary control circuit that may be incorporated into the circular stapler of FIG. 1, in a first state of operation.

As a sequence, FIGS. 23A-23F show the various states of circuit (4100) during operation of instrument (10). In particular, FIG. 23A shows circuit (4100) in a state before battery pack (120) is inserted into handle assembly (10).

Figure 23B:
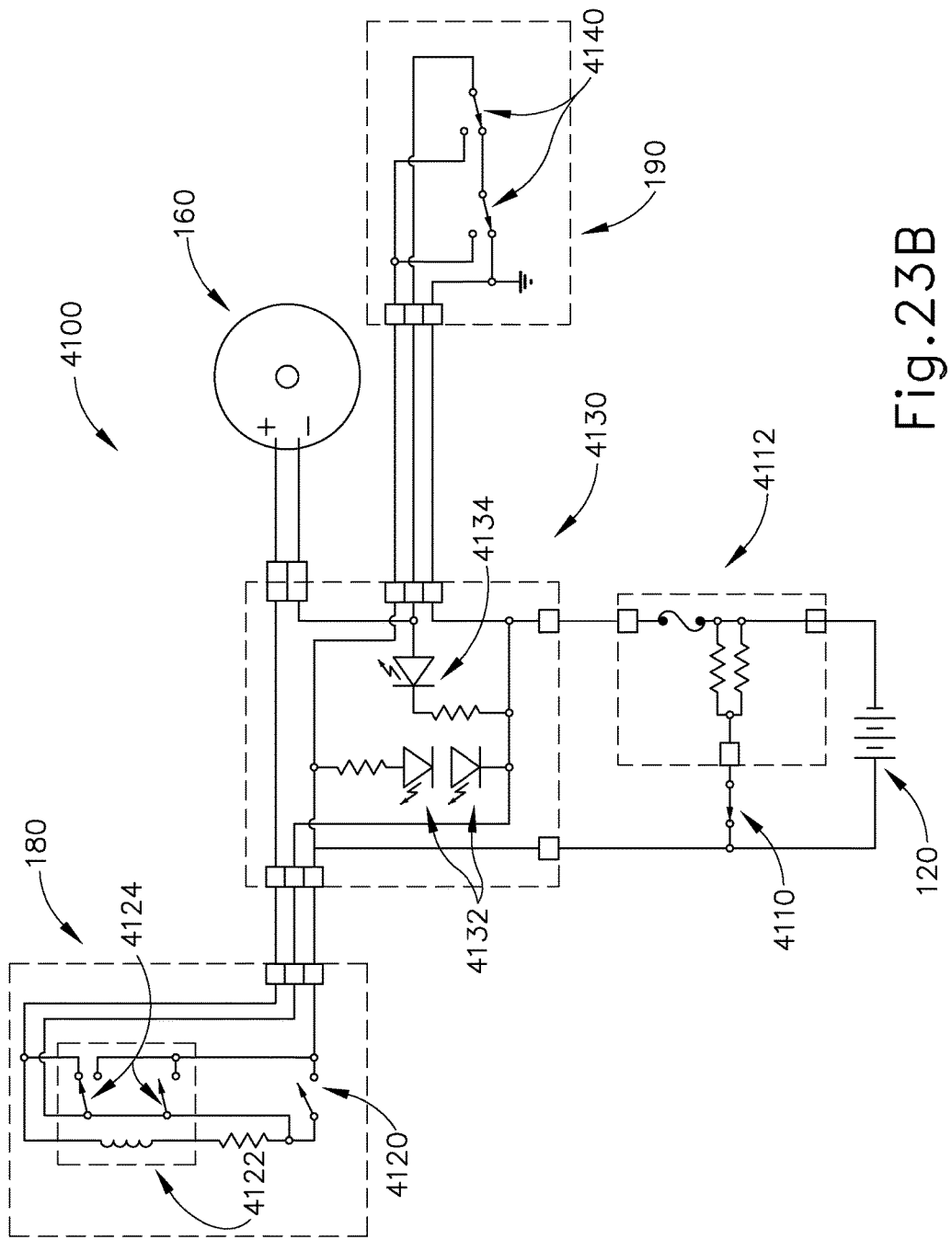
FIG. 23B depicts a schematic view of the control circuit of FIG. 23A, in a second state of operation.

FIG. 23B shows circuit (4100) in a state where battery pack (120) has been inserted into handle assembly (10). The insertion of battery pack (120) into handle assembly (10) has automatically closed switch (4110), such that battery pack (120) is electrically coupled with battery drain module (4112). This corresponds with block (4004) from process (4000) of FIGS. 22A-22B. As noted above, switch (4110) may be closed by insertion of battery pack (120) in accordance with at least some of the teachings of U.S. Patent App. No., entitled "Surgical Stapler with Ready State Indicator," filed on even date herewith, issued as U.S. Pat. No. 10,194,911 on Feb. 5, 2019, the disclosure of which is incorporated by reference herein. It should also be understood that backlight LEDs (4132) may illuminate in response to insertion of battery pack (120) in handle assembly (100).

Figure 23C:
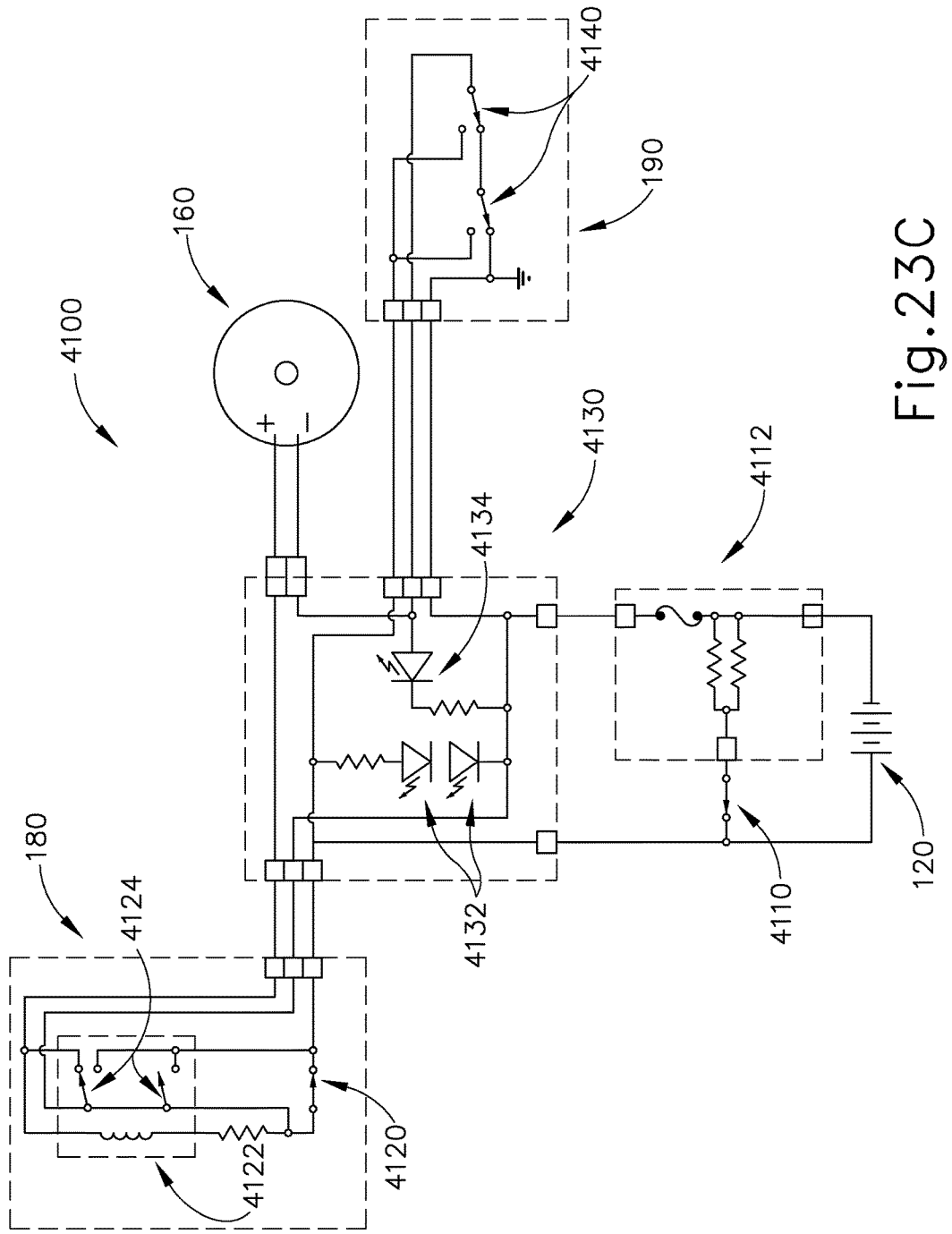
FIG. 23C depicts a schematic view of the control circuit of FIG. 23A, in a third state of operation.
Figure 23D:
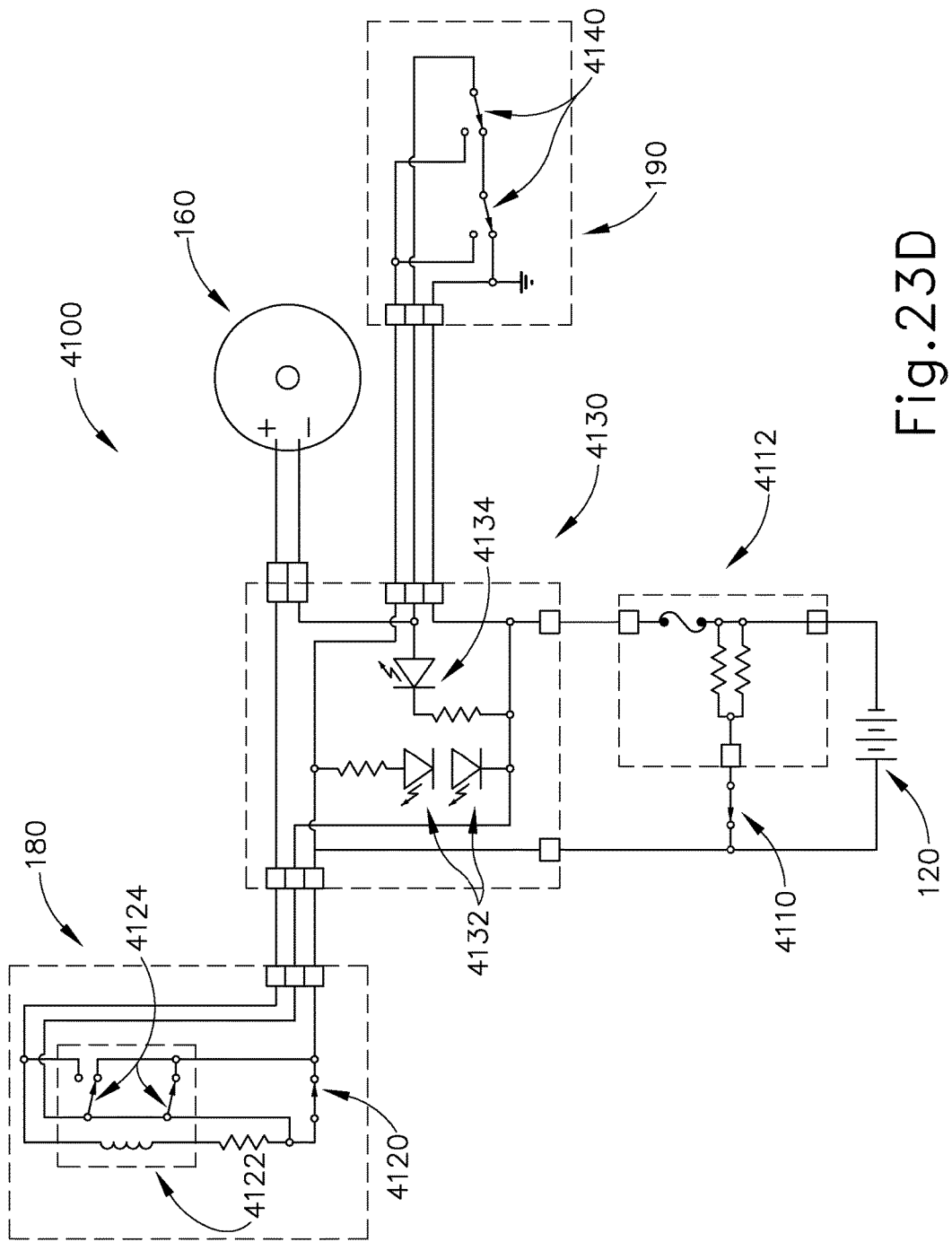
FIG. 23D depicts a schematic view of the control circuit of FIG. 23A, in a fourth state of operation.

FIG. 23C shows circuit (4100) in a state where the operator has actuated firing trigger (150), thereby closing switch (4120). This corresponds with block (4030) from process (4000) of FIGS. 22A-22B. Relay (4122) is configured to automatically and immediately actuate both switches (4124) in response to closure of switch (4120), as shown in FIG. 23D. Such actuation of switches (4124) is provided by relay (4122) through activation of a magnet in response to closure of switch (4120), as is known in the art. Closure of switches (4124) will complete a circuit between battery (120) and motor (160), thereby causing motor (160) to actuate the firing mechanism of stapling head assembly (300) as described above.

Figure 23E:
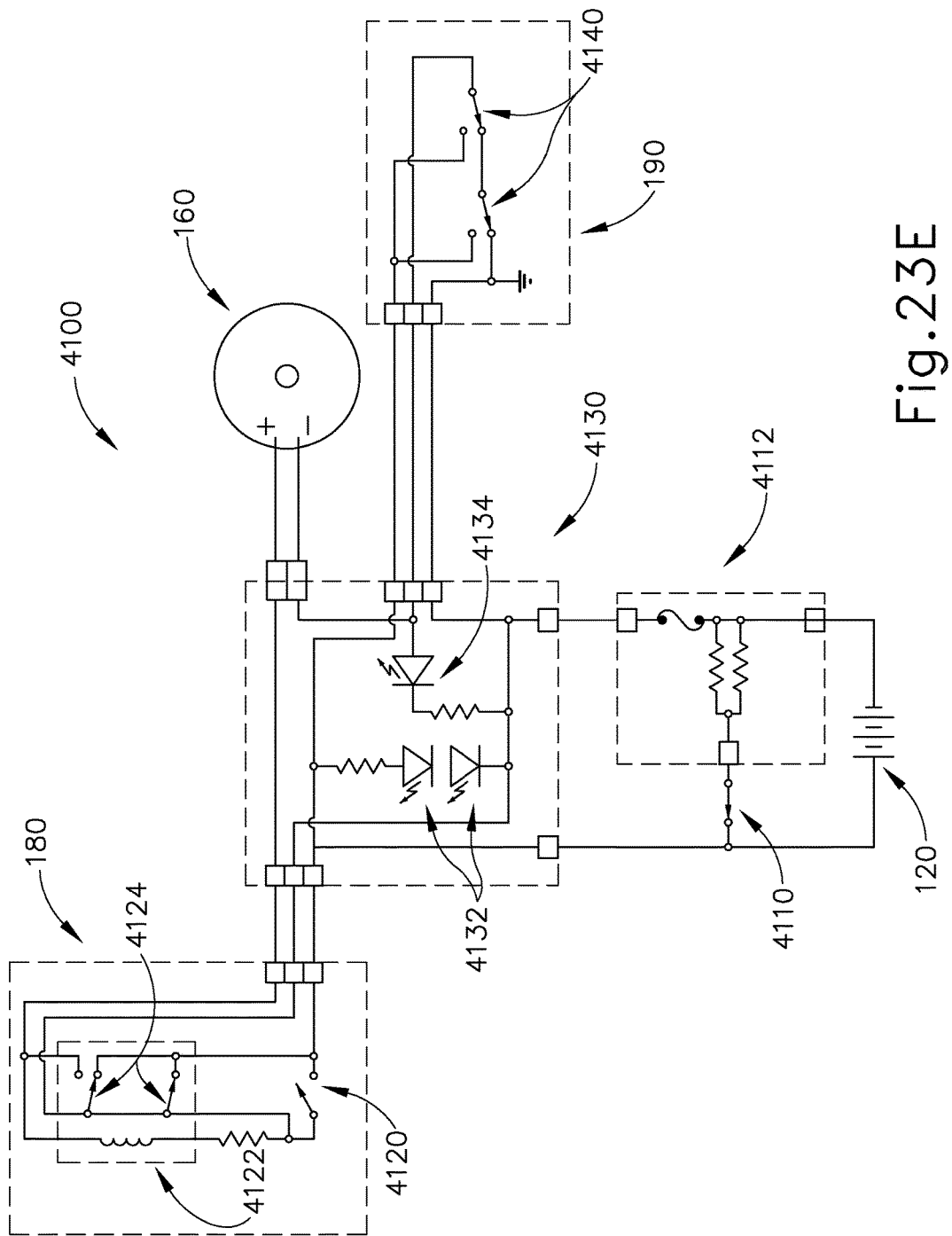
FIG. 23E depicts a schematic view of the control circuit of FIG. 23A, in a fifth state of operation.

Relay (4122) of the present example is configured such that, once switches (4124) are transitioned from the state shown in FIGS. 23A-23C to the state shown in FIG. 23D, switches (4124) will remain in the state shown in FIG. 23D regardless of what subsequently happens with switch (4120). In particular, FIG. 23E shows switch (4120) transitioned back to the open state (e.g., by the operator releasing a grip on firing trigger (150) or intentionally moving trigger (150) back from the position shown in FIG. 12E to the position shown in FIG. 12D, etc.). Despite switch (4120) being transitioned back to the open state as shown in FIG. 23E, switches (4124) remain in the state first shown in FIG. 23D. In other words, switches (4124) maintain completion of the circuit between battery (120) and motor (160), thereby ensuring that motor (160) will complete actuation of the firing mechanism of stapling head assembly (300) even with switch (4120) transitioned back to the open state. Relay (4122) thus provides a commitment to completion of the actuation stroke in accordance with block (4032).

Figure 23F:
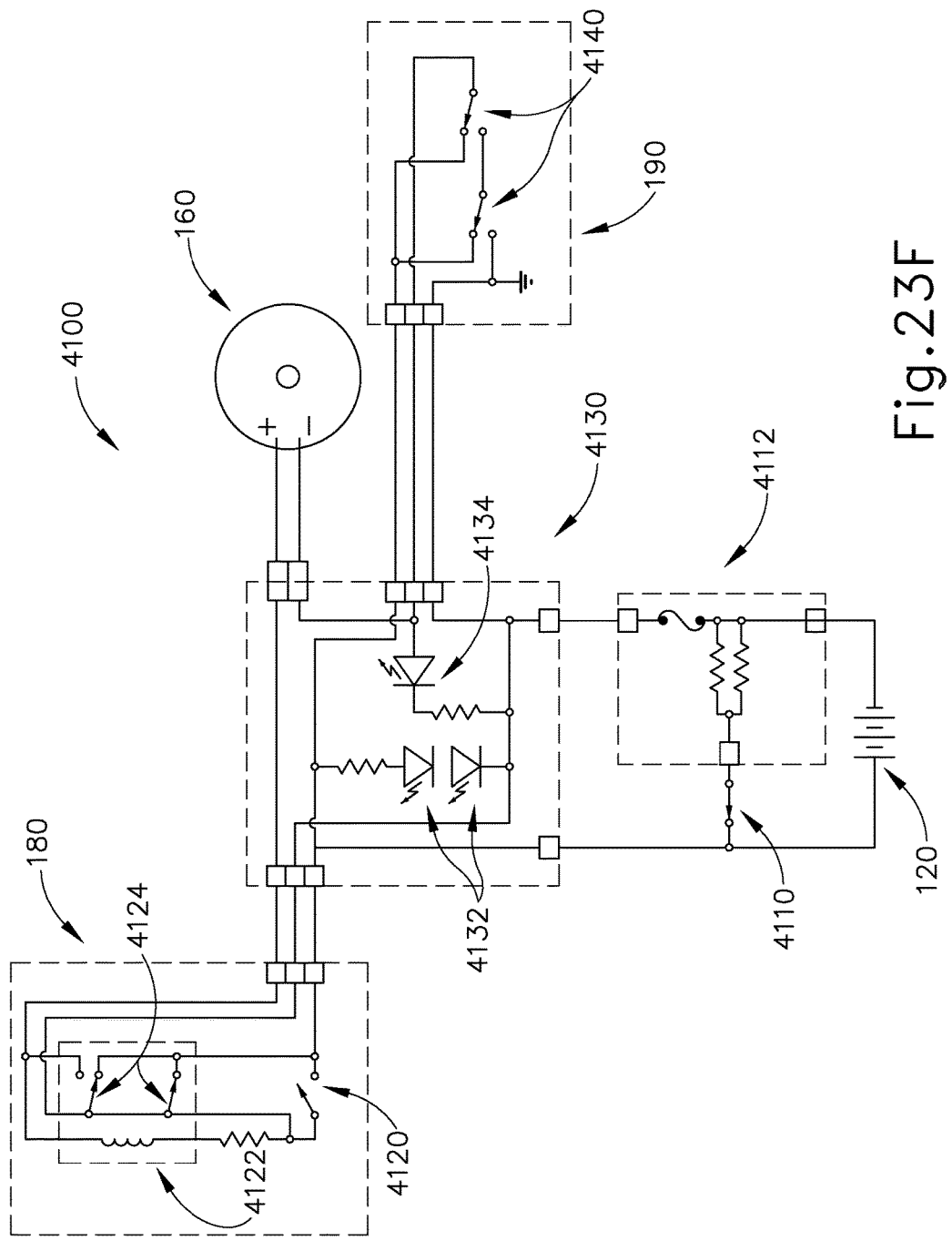
FIG. 23F depicts a schematic view of the control circuit of FIG. 23A, in a sixth state of operation.

FIG. 23F shows circuit (4000) in a state where paddle (806) of rocker member (800) has changed the state of switches (4140). In this state, switches (4140) provide a short for circuit motor (160). In addition to decoupling motor (160) from battery (120), this short circuiting of motor (160) provides a braking effect on motor (160). By way of example only, this effect may be provided in accordance with at least some of the teachings of U.S. Pub. No. 2015/0083774, entitled "Control Features for Motorized Surgical Stapling Instrument," published March 26, 2015, issued as U.S. Pat. No. 9,907,552 on Mar. 6, 2018, the disclosure of which is incorporated by reference herein. At this stage of operation, the operator may translate anvil (400) distally to release tissue from between opposing surfaces (412, 322) of anvil (400) and stapling head assembly (300) and then remove instrument (10) from the patient in accordance with block (4044). In the event that the operator fails to subsequently remove battery pack (120) from handle assembly (100) in accordance with block (4046), battery drain module (4112) will continue to drain power from battery pack (120) until no power is left in battery pack (120). It should also be understood that, since relay (4122) comprises a conventional polarized double pole double throw (DPDT) relay, an operator may not successfully cause motor (160) to operate in reverse simply by reversing the polarity of the voltage applied to motor (160) via relay (4122).

Figure 24:
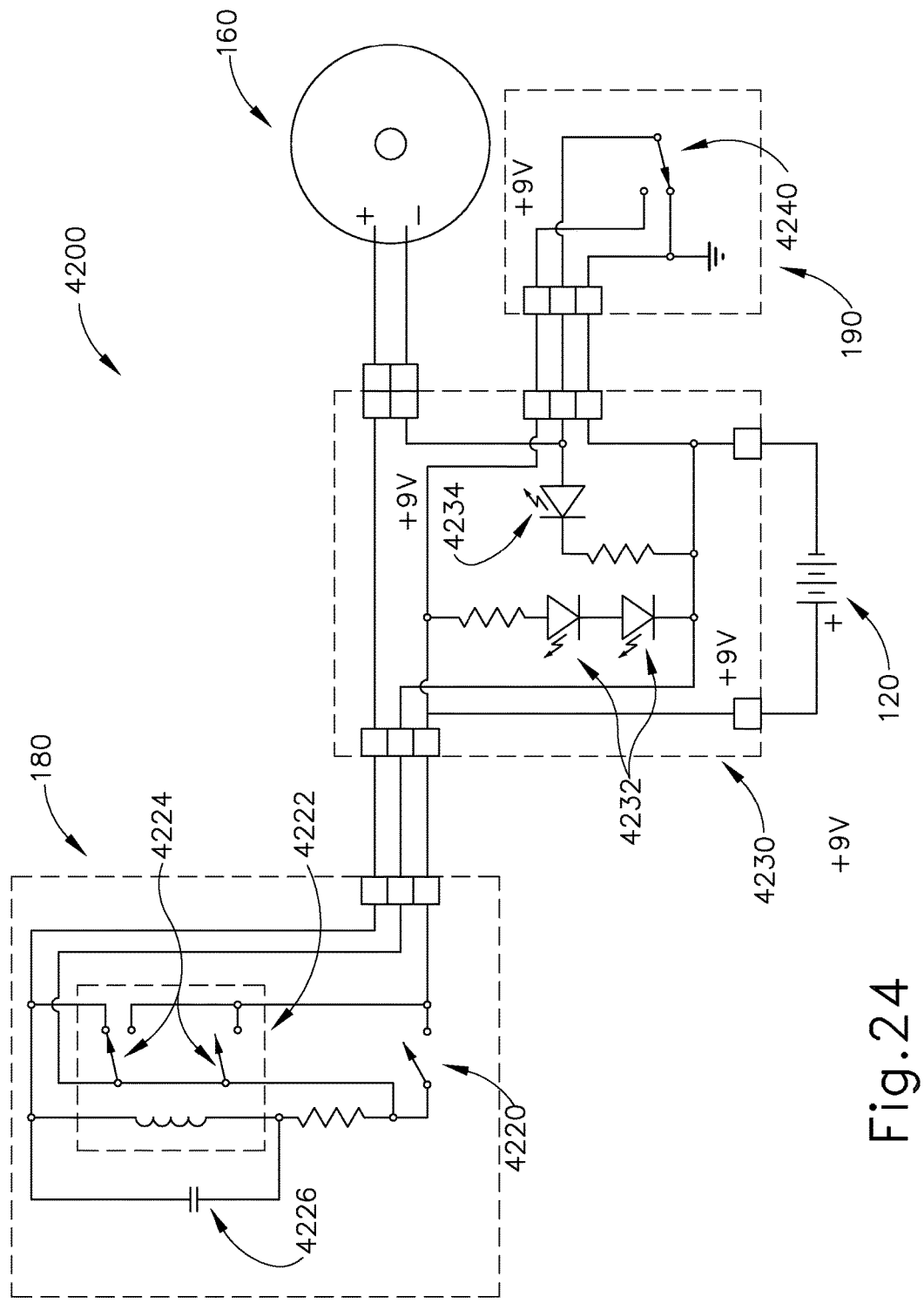
FIG. 24 depicts a schematic view of an exemplary alternative control circuit that may be incorporated into the circular stapler of FIG. 1.

FIG. 24 shows another exemplary circuit (4200), which is a merely illustrative variation of circuit (4100). Circuit (4200) of this example thus also includes components that may be incorporated into motor activation module (180) and short circuit module (190). Circuit (4200) further includes battery pack (120), motor (160), and a feedback module (4230). While circuit (4200) of this example lacks a battery drain module, it should be understood that a battery drain module (similar to a battery drain module (4112) or otherwise configured) may be readily incorporated into circuit (4200).

Short circuit module (190) of circuit (4200) is substantially identical to short circuit module (190) of circuit (4100) except that short circuit module (190) of circuit (4200) includes just one switch (4240) instead of two switches (4140). Feedback module (4230) of circuit (4200) is substantially identical to feedback module (4130) of circuit (4100). In particular, feedback module (4230) of circuit (4200) includes a pair of backlight light emitting diodes (LEDs) (4232) and an indicator LED (4234). LEDs (4232, 4234) are configured and operable just like LEDs (4132, 4134) of circuit (4100).

Motor activation module (180) of circuit (4200) is substantially identical to motor activation module (180) of circuit (4100). In particular, motor activation module (180) of circuit (4200) includes a switch (4220) and a relay (4222). Switch (4220) is configured to be closed by paddle (158) of firing trigger (150) when firing trigger (150) is pivoted from the position shown in FIG. 12D to the position shown in FIG. 12E. Relay (4222) comprises a conventional double pole double throw (DPDT) relay, such that relay (4222) includes a pair of integral switches (4224). As described above with respect to relay (4122), relay (4222) of circuit (4200) provides a commitment to completion of the actuation stroke in accordance with block (4032) of FIGS. 22A-22B. In particular, once switch (4120) is actuated by paddle (158) of firing trigger (150), switches (4224) maintain completion of the circuit between battery (120) and motor (160), thereby ensuring that motor (160) will complete actuation of the firing mechanism of stapling head assembly (300) even if switch (4220) is transitioned back to the open state.

Unlike motor activation module (180) of circuit (4100), motor activation module (180) of circuit (4200) further includes a hold-up capacitor (4226). Hold-up capacitor (4226) is applied across the electromechanical coil of relay (4222). Hold-up capacitor (4226) is configured to prevent mechanical shock from impacting the performance of relay (4222). For instance, as noted above, some versions of anvil (400) include a breakable washer within annular recess (418). This washer is broken by knife member (340) when knife member (340) completes a full distal range of motion from the position shown in FIG. 21C to the position shown in FIG. 21D. When knife member (340) breaks the washer, this breakage of the washer may provide a mechanical shock (e.g., similar to a mechanical shock encountered when a piece of rigid plastic is broken). This mechanical shock may be communicated along shaft assembly (200) to components in handle assembly (100). In instances, this mechanical shock may tend to jar one or both switches (4224) back to the open state, which may disrupt completion of the firing stroke. Even in the presence of such mechanical shock, hold-up capacitor (4226) may maintain activation of relay (4222), maintaining power to motor (160) and thereby ensuring undisturbed completion of the firing stroke.

B. Exemplary Transistor-Based Control Circuit for Surgical Stapler

Figure 25:
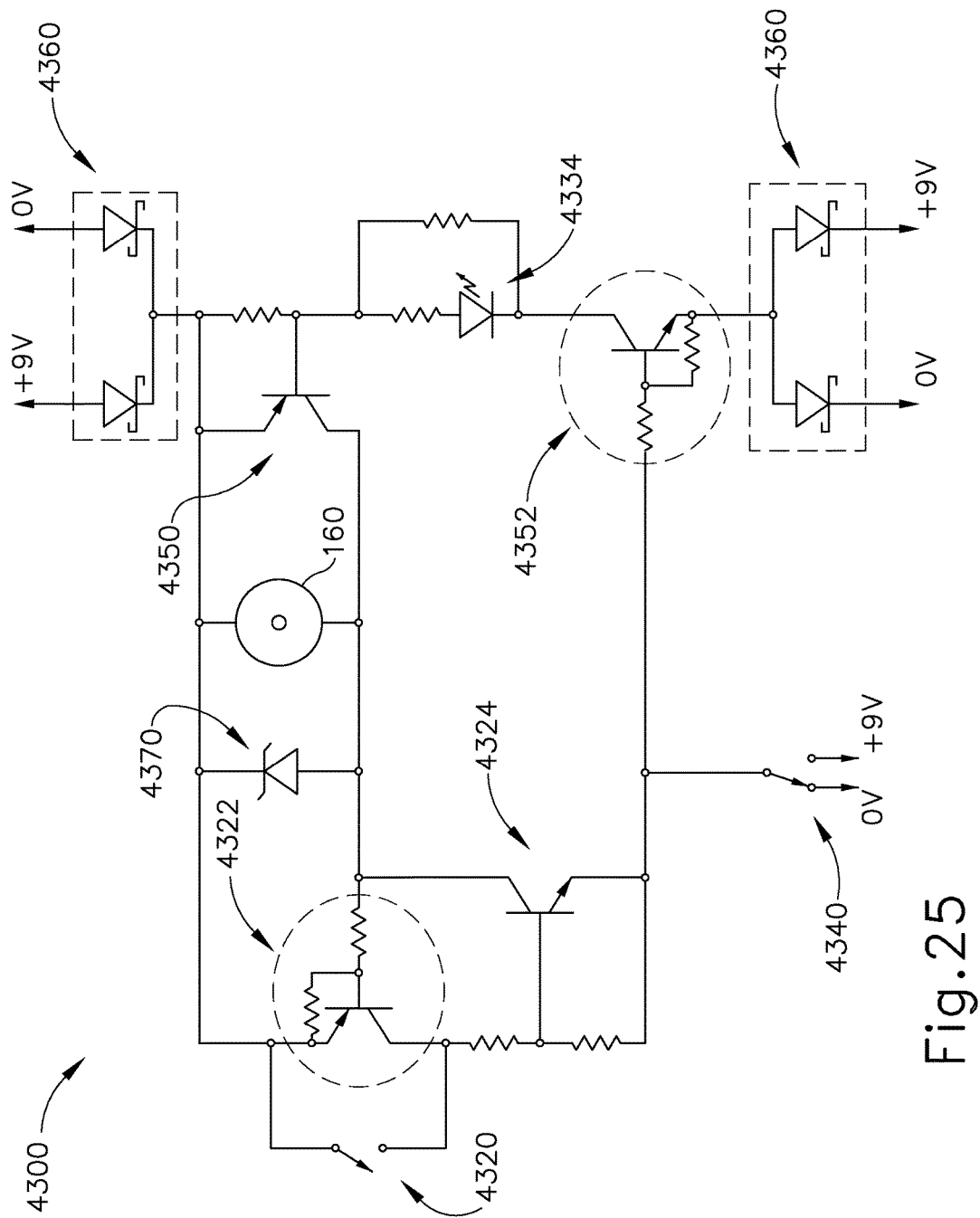
FIG. 25 depicts a schematic view of another exemplary alternative control circuit that may be incorporated into the circular stapler of FIG. 1.

FIG. 25 shows another exemplary circuit (4300) that may be readily incorporated into instrument (10). In particular, circuit (4300) includes components that may be incorporated into motor activation module (180) and short circuit module (190). Circuit (4300) comprises a firing switch (4320), a stop switch (4340), a set of bipolar transistors (4322, 4324, 4350, 4352), and an indicator LED (4334). Circuit (4300) is in communication with battery pack (not shown in FIG. 25) via two sets of dual schottky diodes (4360). Diodes (4360) maintain current flow in a single direction.

Firing switch (4320) is configured to be closed by paddle (158) of firing trigger (150) when firing trigger (150) is pivoted from the position shown in FIG. 12D to the position shown in FIG. 12E. By way of example only, switch (4320) may comprise a single pole single throw (SPST) momentary tactile switch. Alternatively, switch (4320) may take any other suitable form. Stop switch (4340) is configured to be actuated by paddle (806) of rocker member (800) when rocker member is pivoted from the position shown in FIGS. 19A and 20A-20C to the position shown in FIGS. 19B and 20D.

Latching transistor (4322) is configured to provide a function similar to that provided by relays (4122, 4222) described above. In particular, latching transistor (4322) is configured to cooperate with a driver transistor (4324) to activate motor (160) in response to closure of firing switch (4320); and to maintain activation of motor (160) through the completion of the firing stroke even in the event that firing switch (4320) transitions back to an open state prior to completion of the firing stroke. In other words, latching transistor (4322) provides a commitment to completion of the actuation stroke in accordance with block (4032) of FIGS. 22A-22B. Various suitable ways in which transistors (4322, 4324) may be constructed and operable will be apparent to those of ordinary skill in the art in view of the teachings herein. A snubber diode (4370) further provides a current path for motor generated voltage. Snubber diode (4370) thus snubs or limits the voltage that the rest of circuit (4300) might otherwise be exposed to. It should be understood that power interruptions will not cause behavioral anomalies in circuit (4300). For instance, power interruptions may be due to high current draws such as those caused by a weak battery or electrical contacts that are not being fully contacted. Such interruptions may have a duration that is less than a second, and in some cases milliseconds.

Stop switch (4340) is configured to activate a motor brake transistor (4350) and a motor brake pre-driver transistor (4352) to provide braking of motor (160) upon completion of the firing stroke as described above. Various suitable ways in which transistors (4350, 4352) may be constructed and operable will be apparent to those of ordinary skill in the art in view of the teachings herein.

Figure 26:
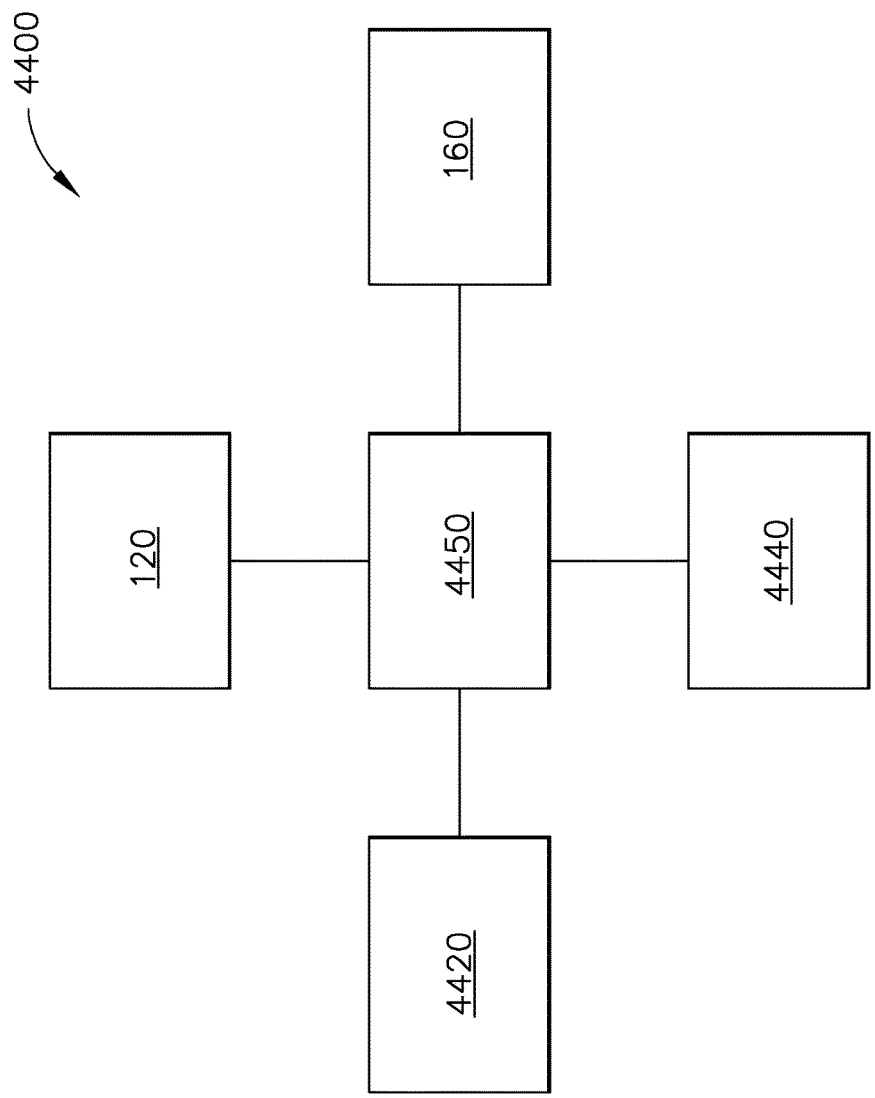
FIG. 26 depicts a schematic view of another exemplary alternative control circuit that may be incorporated into the circular stapler of FIG. 1.

Indicator LED (4334) is configured to illuminate, change color, or otherwise react to an operational condition associated with instrument (10). For instance, indicator LED (4334) may be configured to provide visual feedback indicating whether anvil (400) is fully coupled with trocar (330). Indicator LED (4334) may thus be in communication with anvil (400) detection features such as those taught in U.S. Patent App. No., entitled "Surgical Stapler with Anvil Seating Detection," filed on even date herewith, issued as U.S. Pat. No. 10,307,157 on Jun. 4, 2019, the disclosure of which is incorporated by reference herein. In addition or in the alternative, indicator LED (4334) may be configured to provide visual feedback indicating whether stapling head assembly (300) is in a ready to fire state. Indicator LED (4334) may thus be in communication with anvil (400) features such as those taught in U.S. Patent App. No., entitled "Surgical Stapler with Ready State Indicator," filed on even date herewith, issued as U.S. Pat. No. 10,194,911 on Feb. 5, 2019, the disclosure of which is incorporated by reference herein. In addition or in the alternative, indicator LED (4334) may be configured to provide visual feedback indicating whether anvil (400) has been sufficiently advanced away from stapling head assembly (300) after a firing stapling head assembly (300) has been actuated and before instrument (10) is removed from the patient. Indicator LED (4334) may thus be in communication with anvil (400) position detection features such as those taught in U.S. Patent App. No., entitled "Surgical Stapler with Anvil State Indicator," filed on even date herewith, issued as U.S. Pat. No. 10,188,386 on Jan. 29, 2019, the disclosure of which is incorporated by reference herein. In addition or in the alternative, indicator LED (4334) may be configured to provide visual feedback indicating a level of stress within the firing mechanism for stapling head assembly (300) and/or indicating whether stapling head assembly (300) has been fully actuated. Indicator LED (4334) may thus be in communication with sensing (330). Indicator LED (4334) may thus be in communication components such as those taught in U.S. Patent App. No., entitled "Surgical Stapler with Incomplete Firing Indicator," filed on even date herewith, issued as U.S. Pat. No. 10,265,066 on Apr. 23, 2019, the disclosure of which is incorporated by reference herein. Still other conditions that may be indicated through indicator LED (4334) will be apparent to those of ordinary skill in the art in view of the teachings herein. It should also be understood that circuit (4300) may include any suitable number of indicator LEDs (4334); or may simply lack an indicator LED (4334) altogether, C. Exemplary Microprocessor-Based Control Circuit for Surgical Stapler FIG. 26 shows another exemplary circuit (4400) that may be readily incorporated into instrument (10). In particular, circuit (4400) includes battery pack (120), motor (160), a firing switch (4420), a stop switch (4440), and a microprocessor (4450). Firing switch (4420) is configured to be closed by paddle (158) of firing trigger (150) when firing trigger (150) is pivoted from the position shown in FIG. 12D to the position shown in FIG. 12E. By way of example only, switch (4420) may comprise a single pole single throw (SPST) momentary tactile switch. Alternatively, switch (4420) may take any other suitable form. Stop switch (4440) is configured to be actuated by paddle (806) of rocker member (800) when rocker member is pivoted from the position shown in FIGS. 19A and 20A-20C to the position shown in FIGS. 19B and 20D.

Microprocessor (4450) is configured to serve as a central hub for the other components of circuit (4400). In addition, microprocessor (4450) is programmed to activate motor (160) in response to closure of firing switch (4420); and to maintain activation of motor (160) through the completion of the firing stroke even in the event that firing switch (4420) transitions back to an open state prior to completion of the firing stroke. In other words, microprocessor (4450) provides a commitment to completion of the actuation stroke in accordance with block (4032) of FIGS. 22A-22B. Microprocessor (4450) is also configured to provide braking of motor (160) upon completion of the firing stroke as described above. Microprocessor (4450) thus provides a single, comprehensive alternative to relays (4122, 4222) and transistors (4322, 4324, 4350, 4352) as described above. Various suitable ways in which microprocessor (4450) may be constructed and operable will be apparent to those of ordinary skill in the art in view of the teachings herein. In some versions, microprocessor (4450) is configured in accordance with, operable in accordance with, and/or placed in an arrangement with other components in accordance with at least some of the teachings of U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising: (a) a body; (b) a shaft assembly extending distally from the body; (c) a stapling head assembly located at the distal end of the shaft assembly, wherein the stapling head assembly is operable to drive an annular array of staples through tissue; (d) an anvil, wherein the anvil is configured to cooperate with the stapling head assembly to deform staples driven through tissue by the stapling head assembly; (e) a firing assembly, wherein the firing assembly is operable to actuate the stapling head assembly to drive the annular array of staples toward the anvil; (f) a motor, wherein the motor is operable to actuate the firing assembly through an actuation stroke to thereby actuate the stapling head assembly; (g) a user input feature, wherein the user input feature is operable transition between an actuated state and a non-actuated state; and (h) an electrical circuit in communication with the user input feature and with the motor, wherein the electrical circuit comprises: (i) a trigger switch, wherein the trigger switch is configured to transition from an open state to a closed state in response to the user input feature transitioning from the non-actuated state to the actuated state, wherein the electrical circuit is configured to activate the motor in response to closure of the trigger switch, and (ii) an electrical latching feature operable to maintain activation of the motor to complete the actuation stroke even if the trigger switch is transitioned back to the open state before completion of the actuation stroke.

EXAMPLE 2

The surgical instrument of Example 1, wherein the electrical latching feature comprises a transistor.

EXAMPLE 3

The surgical instrument of Example 1, wherein the electrical latching feature comprises a microprocessor.

EXAMPLE 4

The surgical instrument of Example 1, wherein the electrical latching feature comprises a relay.

EXAMPLE 5

The surgical instrument of Example 4, wherein the relay comprises a double pole double throw relay.

EXAMPLE 6

The surgical instrument of any one or more of Examples 4 through 5, wherein the electrical circuit further comprises a hold-up capacitor coupled with the relay.

EXAMPLE 7

The surgical instrument of any one or more of Examples 1 through 6, wherein the electrical circuit further comprises a short circuit module, wherein the short circuit module is configured to provide a short circuit to the motor in response to completion of the actuation stroke.

EXAMPLE 8

The surgical instrument of Example 7, wherein the short circuit module comprises a short circuit switch, wherein the short circuit switch is configured to transition between a first state and a second state, wherein the short circuit switch is configured to provide the short circuit when the short circuit switch is transitioned to the second state.

EXAMPLE 9

The surgical instrument of Example 8, further comprising a deactivation member, wherein the deactivation member is configured to transition between an actuated state and a non-actuated state, wherein the deactivation member is configured to maintain the non-actuated state during the activation stroke, wherein the deactivation member is configured to transition from the non-actuated state to the actuated state in response to completion of the actuation stroke, wherein the deactivation member is configured to transition the short circuit switch from the first state to the second state in response to the deactivation member being transitioned to the actuated state.

EXAMPLE 10

The surgical instrument of Example 9, wherein the firing assembly comprises a movable member configured to engage the deactivation member upon completion of the firing stroke to thereby transition the deactivation member from the non-actuated state to the actuated state.

EXAMPLE 11

The surgical instrument of any one or more of Examples 1 through 10, wherein the user input feature comprises a trigger pivotably coupled with the body, wherein the trigger is pivotable from a first position to a second position to thereby transition from the non-actuated state to the actuated state.

EXAMPLE 12

The surgical instrument of Example 11, wherein the trigger comprises a paddle, wherein the paddle is configured to engage the trigger switch to thereby transition the trigger switch from the open state to the closed state in response to pivoting of the trigger from the first position to the second position

EXAMPLE 13

The surgical instrument of Example 12, wherein the paddle is configured to disengage the trigger switch in response to pivoting of the trigger from the second position to the first position.

EXAMPLE 14

The surgical instrument of any one or more of Examples 1 through 13, wherein the firing assembly comprises a translating member extending through the shaft assembly, wherein the translating member is configured to translate distally through the shaft assembly during a first portion of the actuation stroke, wherein the translating member is configured to translate proximally through the shaft assembly during a second portion of the actuation stroke.

EXAMPLE 15

The surgical instrument of Example 14, wherein the stapling head assembly comprises a staple driver and a tissue cutting member, wherein the translating member is configured to drive the staple driver and the tissue cutting member distally during the first portion of the actuation stroke, wherein the translating member is configured to drive the staple driver and the tissue cutting member proximally during the second portion of the actuation stroke.

EXAMPLE 16

The surgical instrument of any one or more of Examples 1 through 15, wherein the electrical circuit further comprises a user feedback feature configured to indicate completion of the firing stroke.

EXAMPLE 17

The surgical instrument of Example 16, wherein the user feedback feature comprises a light emitting diode.

EXAMPLE 18

The surgical instrument of any one or more of Examples 1 through 17, further comprising a battery, wherein the battery is configured to provide electrical power to the motor via the electrical circuit, wherein the electrical circuit further comprises a battery drain module, wherein the battery drain module is configured to drain power from the battery after completion of the actuation stroke.

EXAMPLE 19

A surgical instrument comprising: (a) a body; (b) a shaft assembly extending distally from the body; (c) a stapling head assembly located at the distal end of the shaft assembly, wherein the stapling head assembly is operable to drive an annular array of staples through tissue; (d) an anvil, wherein the anvil is configured to cooperate with the stapling head assembly to deform staples driven through tissue by the stapling head assembly; (e) a firing assembly, wherein the firing assembly is operable to actuate the stapling head assembly to drive the annular array of staples toward the anvil; (f) a motor, wherein the motor is operable to actuate the firing assembly through an actuation stroke to thereby actuate the stapling head assembly; (g) a trigger pivotably coupled with the body, wherein the trigger is operable to pivot between a first position and a second position; and (h) an electrical circuit in communication with the user input feature and with the motor, wherein the electrical circuit comprises: (i) a trigger switch, wherein the trigger is configured to engage the trigger switch to thereby transition the trigger switch from an open state to a closed state in response to pivoting of the trigger from the first position to the second position, wherein the trigger is configured to disengage the trigger switch in response to pivoting of the trigger from the second position to the first position, wherein the electrical circuit is configured to activate the motor in response to closure of the trigger switch, and (ii) a control feature operable to maintain activation of the motor to complete the actuation stroke even if the trigger switch is transitioned back to the open state before completion of the actuation stroke.

EXAMPLE 20

A method of operating a surgical stapling instrument, wherein the instrument comprises: (a) a stapling head assembly, wherein the stapling head assembly is operable to drive an annular array of staples through tissue; (b) an anvil, wherein the anvil is configured to cooperate with the stapling head assembly to deform staples driven through tissue by the stapling head assembly; (c) a firing assembly, wherein the firing assembly is operable to actuate the stapling head assembly to drive the annular array of staples toward the anvil; (d) a motor, wherein the motor is operable to actuate the firing assembly through an actuation stroke to thereby actuate the stapling head assembly; and (e) a user input feature, wherein the user input feature is operable transition between an actuated state and a non-actuated state; wherein the method comprises: (a) actuating the user input feature to thereby transition the user input feature from the non-actuated state to the actuated state, wherein the act of actuating the user input feature comprises closing a trigger switch; (b) activating the motor in response to closure of the trigger switch, wherein activation of the motor initiates the actuation stroke; (c) opening the trigger switch; (d) maintaining activation of the motor to complete the actuation stroke after the trigger switch is opened; and (e) de-activating the motor upon completion of the actuation stroke.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,573,573on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783, Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a shaft assembly extending distally from the body;
   (c) a stapling head assembly located at the distal end of the shaft assembly, wherein the stapling head assembly is operable to drive an annular array of staples through tissue;
   (d) an anvil, wherein the anvil is configured to cooperate with the stapling head assembly to deform staples driven through tissue by the stapling head assembly;
   (e) a firing assembly, wherein the firing assembly is operable to actuate the stapling head assembly to drive the annular array of staples toward the anvil;
   (f) a motor, wherein the motor is operable to actuate the firing assembly through an actuation stroke to thereby actuate the stapling head assembly;
   (g) a user input feature, wherein the user input feature is operable to move relative to the body to thereby transition between an actuated state and a non-actuated state, wherein the user input feature is further operable to move from the non-actuated state to the actuated state during the actuation stroke; and
   (h) an electrical circuit in communication with the motor, wherein the electrical circuit comprises:
      (i) a trigger switch, wherein the trigger switch is configured to transition from an open state to a closed state in response to the user input feature transitioning from the non-actuated state to the actuated state, wherein the electrical circuit is configured to activate the motor in response to closure of the trigger switch, wherein the trigger switch is further configured to transition back to the open state after reaching the closed state in response to the user input feature transitioning from the actuated state back to the non-actuated state, and (ii) an electrical latching feature operable to maintain activation of the motor to complete the actuation stroke even if the trigger switch is transitioned back to the open state before completion of the actuation stroke.

2. The surgical instrument of claim 1, wherein the electrical latching feature comprises a transistor.

3. The surgical instrument of claim 1, wherein the electrical latching feature comprises a microprocessor.

4. The surgical instrument of claim 1, wherein the electrical latching feature comprises a relay.

5. The surgical instrument of claim 4, wherein the relay comprises a double pole double throw relay.

6. The surgical instrument of claim 4, wherein the electrical circuit further comprises a hold-up capacitor coupled with the relay.

7. The surgical instrument of claim 1, wherein the electrical circuit further comprises a short circuit module, wherein the short circuit module is configured to provide a short circuit to the motor in response to completion of the actuation stroke.

8. The surgical instrument of claim 7, wherein the short circuit module comprises a short circuit switch, wherein the short circuit switch is configured to transition between a first state and a second state, wherein the short circuit switch is configured to provide the short circuit when the short circuit switch is transitioned to the second state.

9. The surgical instrument of claim 8, further comprising a deactivation member, wherein the deactivation member is configured to transition between an actuated state and a non-actuated state, wherein the deactivation member is configured to maintain the non-actuated state during the activation stroke, wherein the deactivation member is configured to transition from the non-actuated state to the actuated state in response to completion of the actuation stroke, wherein the deactivation member is configured to transition the short circuit switch from the first state to the second state in response to the deactivation member being transitioned to the actuated state.

10. The surgical instrument of claim 9, wherein the firing assembly comprises a movable member configured to engage the deactivation member upon completion of the firing stroke to thereby transition the deactivation member from the non-actuated state to the actuated state.

11. The surgical instrument of claim 1, wherein the user input feature comprises a trigger pivotably coupled with the body, wherein the trigger is pivotable from a first position to a second position to thereby transition from the non-actuated state to the actuated state.

12. The surgical instrument of claim 11, wherein the trigger comprises a paddle, wherein the paddle is configured to engage the trigger switch to thereby transition the trigger switch from the open state to the closed state in response to pivoting of the trigger from the first position to the second position.

13. The surgical instrument of claim 12, wherein the paddle is configured to disengage the trigger switch in response to pivoting of the trigger from the second position to the first position.

14. The surgical instrument of claim 1, wherein the firing assembly comprises a translating member extending through the shaft assembly, wherein the translating member is configured to translate distally through the shaft assembly during a first portion of the actuation stroke, wherein the translating member is configured to translate proximally through the shaft assembly during a second portion of the actuation stroke.

15. The surgical instrument of claim 14, wherein the stapling head assembly comprises a staple driver and a tissue cutting member, wherein the translating member is configured to drive the staple driver and the tissue cutting member distally during the first portion of the actuation stroke, wherein the translating member is configured to drive the staple driver and the tissue cutting member proximally during the second portion of the actuation stroke.

16. The surgical instrument of claim 1, wherein the electrical circuit further comprises a user feedback feature configured to indicate completion of the firing stroke.

17. The surgical instrument of claim 16, wherein the user feedback feature comprises a light emitting diode.

18. The surgical instrument of claim 1, further comprising a battery, wherein the battery is configured to provide electrical power to the motor via the electrical circuit, wherein the electrical circuit further comprises a battery drain module, wherein the battery drain module is configured to drain power from the battery after completion of the actuation stroke.

19. A surgical instrument comprising:

(a) a body;

(b) a shaft assembly extending distally from the body;

(c) a stapling head assembly located at the distal end of the shaft assembly, wherein the stapling head assembly is operable to drive an annular array of staples through tissue;

(d) an anvil, wherein the anvil is configured to cooperate with the stapling head assembly to deform staples driven through tissue by the stapling head assembly;

(e) a firing assembly, wherein the firing assembly is operable to actuate the stapling head assembly to drive the annular array of staples toward the anvil;

(f) a motor, wherein the motor is operable to actuate the firing assembly through an actuation stroke to thereby actuate the stapling head assembly;

(g) a trigger pivotably coupled with the body, wherein the trigger is operable to pivot between a first position and a second position, wherein the trigger is further operable to pivot back to the first position from the second position during the actuation stroke; and (h) an electrical circuit in communication and with the motor, wherein the electrical circuit comprises:

(i) a trigger switch, wherein the trigger is configured to engage the trigger switch to thereby transition the trigger switch from an open state to a closed state in response to pivoting of the trigger from the first position to the second position, wherein the trigger is configured to disengage the trigger switch in response to pivoting of the trigger from the second position to the first position, wherein the electrical circuit is configured to activate the motor in response to closure of the trigger switch, and (ii) a control feature operable to maintain activation of the motor to complete the actuation stroke even if the trigger switch is transitioned back to the open state before completion of the actuation stroke.

20. A method of operating a surgical stapling instrument, wherein the instrument comprises:

(a) a stapling head assembly, wherein the stapling head assembly is operable to drive an annular array of staples through tissue;
(b) an anvil, wherein the anvil is configured to cooperate with the stapling head assembly to deform staples driven through tissue by the stapling head assembly;
(c) a firing assembly, wherein the firing assembly is operable to actuate the stapling head assembly to drive the annular array of staples toward the anvil;
(d) a motor, wherein the motor is operable to actuate the firing assembly through an actuation stroke to thereby actuate the stapling head assembly; and
(e) a user input feature, wherein the user input feature is operable transition between an actuated state and a non-actuated state;

wherein the method comprises:
(a) actuating the user input feature to thereby transition the user input feature from the non-actuated state to the actuated state, wherein the act of actuating the user input feature comprises closing a trigger switch;
(b) activating the motor in response to closure of the trigger switch, wherein activation of the motor initiates the actuation stroke;
(c) opening the trigger switch before the actuation stroke is completed;
(d) maintaining activation of the motor to complete the actuation stroke after the trigger switch is opened; and
(e) de-activating the motor upon completion of the actuation stroke.

* * * * *